United States Patent
Kellogg, Jr. et al.

(10) Patent No.: US 11,224,673 B1
(45) Date of Patent: *Jan. 18, 2022

(54) OPERATING ROOM INTELLIGENT PLATFORM AND STERILIZATION SYSTEM

(71) Applicant: SYNERGY MED GLOBAL DESIGN SOLUTIONS, LLC, Golden, CO (US)

(72) Inventors: Sanford M. Kellogg, Jr., Golden, CO (US); Thomas George Hudson, Excelsior, MN (US)

(73) Assignee: SYNERGY MED GLOBAL DESIGN SOLUTIONS, LLC, Golden, CO (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/522,274

(22) Filed: Jul. 25, 2019

Related U.S. Application Data

(63) Continuation-in-part of application No. 16/125,736, filed on Sep. 9, 2018, now Pat. No. 10,369,242, which
(Continued)

(51) Int. Cl.
*A61L 9/00* (2006.01)
*B01D 39/00* (2006.01)
(Continued)

(52) U.S. Cl.
CPC .............. *A61L 2/208* (2013.01); *A61L 2/10* (2013.01); *A61L 2/22* (2013.01); *A61L 2/24* (2013.01);
(Continued)

(58) Field of Classification Search
CPC .. A61L 9/20; A61L 9/16; E04F 13/074; E04B 9/003
(Continued)

(56) References Cited

U.S. PATENT DOCUMENTS

| 6,132,309 A | 10/2000 | Panelli et al. |
| 7,125,332 B2 | 10/2006 | Beaver et al. |

(Continued)

OTHER PUBLICATIONS

Precision Air Products Co., "LifeSuite Surgical Cleanroom", Form SLS004, (c) 2014 Precision Air Products, uploaded from http://www.precisionairproducts.com/docs/LIFESuite2014.pdf on Jul. 17, 2016.

(Continued)

*Primary Examiner* — Monzer R Chorbaji
(74) *Attorney, Agent, or Firm* — Stephen E. Zweig

(57) ABSTRACT

System and method to reduce risk of patient infections (HAI), using operating rooms (chambers) equipped with suitable automatic airborne sterilizing agent generators, sensors, mechanisms, automatic air control devices, and laminar flow devices. After suitable safety checks, the system isolates the interior air from external air, and activates an air phase anti-microbial agent generator, filling the room with an air-phase anti-microbial agent. After sterilization, the invention deactivates the generator then restores the connection to outside sterilized air. The chamber also comprises an intelligent platform comprising video cameras, and computer vision systems configured to identify humans and medical supplies, read optical tags, and correlate recognized objects with RFID tag data. The intelligent platform can be configured to automatically detect and warn on conditions associated with a high risk of HAI, optimize the sterility of the chamber, automatically detect other operating room issues, and interface with outside computerized medical databases and facilities networks.

21 Claims, 12 Drawing Sheets

Related U.S. Application Data is a continuation of application No. 15/236,888, filed on Aug. 15, 2016, now Pat. No. 10,071,177.

(60) Provisional application No. 62/729,326, filed on Sep. 10, 2018.

(51) Int. Cl.

| | |
|---|---|
| *B01L 1/04* | (2006.01) |
| *F24F 9/00* | (2006.01) |
| *A61L 2/20* | (2006.01) |
| *F24F 11/77* | (2018.01) |
| *F24F 11/75* | (2018.01) |
| *A61L 2/10* | (2006.01) |
| *A61L 2/22* | (2006.01) |
| *F24F 11/30* | (2018.01) |
| *A61L 9/20* | (2006.01) |
| *F24F 13/10* | (2006.01) |
| *F24F 7/10* | (2006.01) |
| *A61L 2/24* | (2006.01) |
| *F24F 3/167* | (2021.01) |
| *F24F 120/10* | (2018.01) |
| *F24F 8/22* | (2021.01) |
| *F24F 8/24* | (2021.01) |
| *F24F 8/108* | (2021.01) |
| *F24F 8/167* | (2021.01) |

(52) U.S. Cl.
CPC ............... *A61L 9/20* (2013.01); *F24F 3/167* (2021.01); *F24F 7/10* (2013.01); *F24F 11/30* (2018.01); *F24F 11/75* (2018.01); *F24F 11/77* (2018.01); *F24F 13/10* (2013.01); *A61L 2202/11* (2013.01); *A61L 2202/13* (2013.01); *A61L 2202/14* (2013.01); *A61L 2202/25* (2013.01); *A61L 2209/111* (2013.01); *A61L 2209/135* (2013.01); *A61L 2209/14* (2013.01); *A61L 2209/16* (2013.01); *F24F 8/108* (2021.01); *F24F 8/167* (2021.01); *F24F 8/22* (2021.01); *F24F 8/24* (2021.01); *F24F 2120/10* (2018.01); *F24F 2221/02* (2013.01); *Y02A 50/20* (2018.01)

(58) Field of Classification Search
USPC ............ 422/1, 4, 24, 28, 30, 292, 305–306; 95/90, 273; 454/187, 188, 228; 96/224, 96/227

See application file for complete search history.

(56) References Cited

U.S. PATENT DOCUMENTS

| | | |
|---|---|---|
| 7,186,371 B1 | 3/2007 | Watling |
| 7,317,955 B2 | 1/2008 | McGreevy |
| 7,557,710 B2 | 7/2009 | Sanchez et al. |
| 7,674,440 B2 | 3/2010 | Martin |
| 8,452,615 B2 | 5/2013 | Abri |
| 8,551,399 B2 | 10/2013 | Shannon et al. |
| 9,938,724 B2 * | 4/2018 | Walters .................. H02G 3/263 |
| 10,369,242 B1 * | 8/2019 | Kellogg, Jr. ............ A61L 2/208 |
| 2009/0099862 A1 | 4/2009 | Fireman et al. |
| 2011/0097896 A1 | 4/2011 | Cursetjee et al. |
| 2014/0006943 A1 | 1/2014 | Robbins et al. |
| 2014/0037496 A1 | 2/2014 | Pomeroy et al. |
| 2016/0038624 A1 * | 2/2016 | Krosney .................. A61L 9/20 422/121 |

OTHER PUBLICATIONS

Dimond, Valerie J. "Take over your makeover: Suite suite rennovation" from "Teching out your surgical suite", Healthcare Purchasing News, Apr. 2016, vol. 40 (4)., uploaded from http://mfphd.com/wp-content/uploads/2016/06/mfPHD-HPN-CoverStory-OR-SuiteRenovation0416.pdf on Jul. 17, 2016.

Agarwal et. al., "A Pervasive Computing System for the Operating Room of the Future", Mobile Networks and Applications, vol. 12. Issue 2-3, Mar. 2007 pp. 215-228.

Bardham and Norskov, "A Context-aware Patient Safety System for the Operating Room", UbiComp'08, Sep. 21-24, 2008, Seoul, Korea.

* cited by examiner

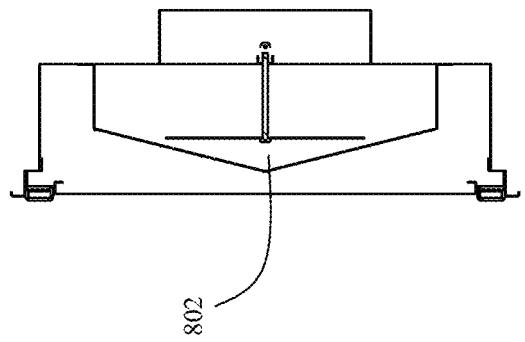
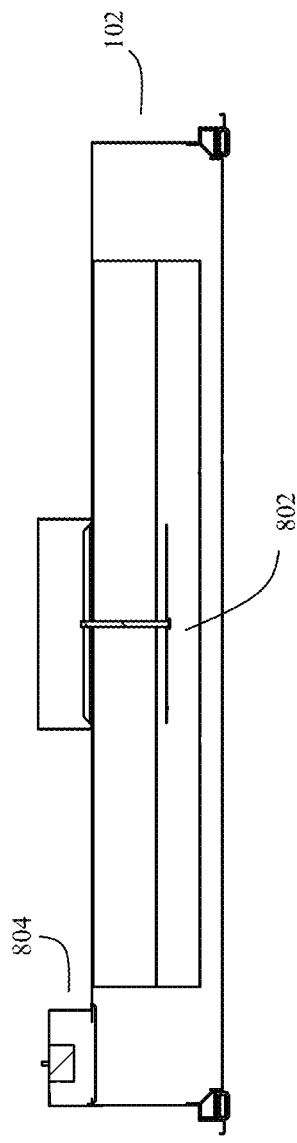
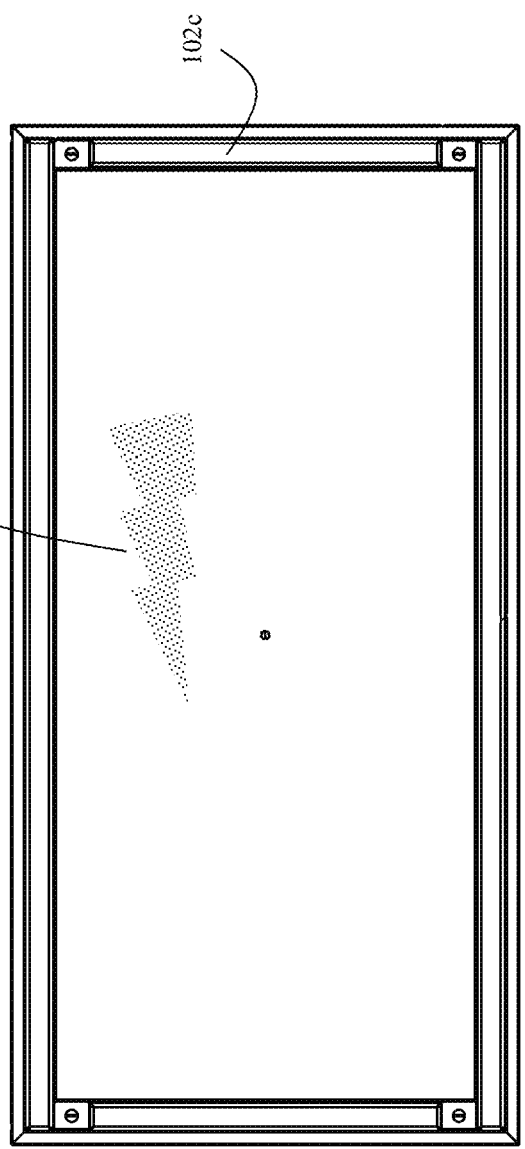

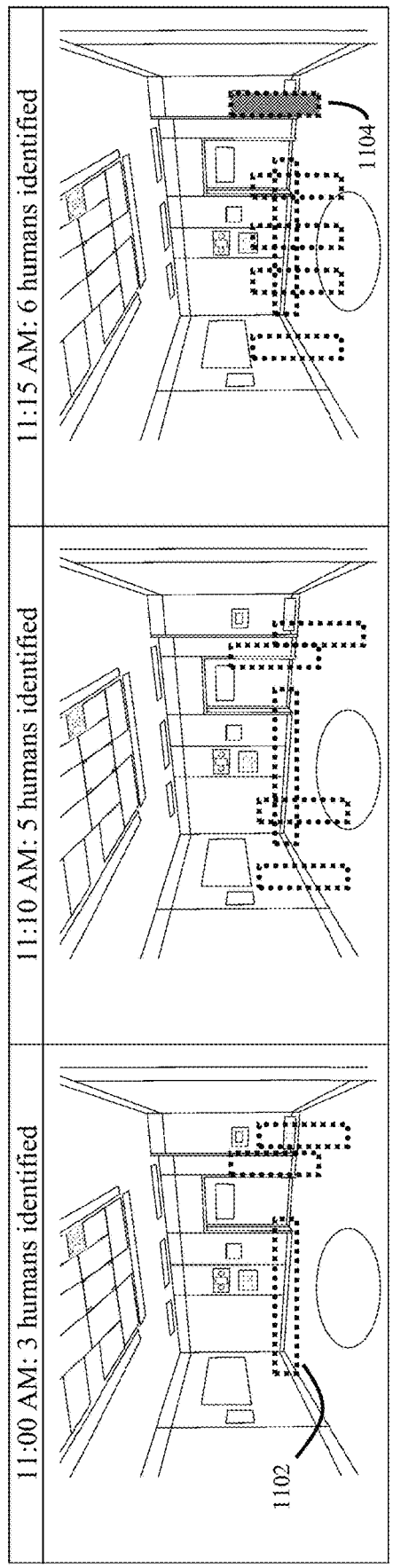

| Time | 11:00 | 11:10 | 11:15 | 11:20 | 11:25 |
|---|---|---|---|---|---|
| Humans present | | | | | |
| Patient: ID 123 | on table | on table | on table | on table | on table |
| Surgeon 1 (Dr. X) | - | enter | by table head | by table head | by table foot |
| Anesth. 1 (Dr. Y) | enter | at AN station | at AN station | at AN station | at AN station |
| Nurse 1 (Ms. A) | enter | at n1 station | at n1 station | at n1 station | at n1 station |
| Nurse 2 (Ms. B) | - | enter | at n2 station | present | present |
| Unknown | - | - | enter | at n2 station | by table head |
| Devices present | | | | | |
| Tool A: ID #4567 | not visible | not visible | by n1 station | at patient | waste container |
| Unknown tool | not present | not present | enter | at n2 station | by table head |

OPERATING ROOM INTELLIGENT PLATFORM AND STERILIZATION SYSTEM

CROSS REFERENCE TO RELATED APPLICATIONS

This application is a continuation in part of U.S. patent application Ser. No. 16/125,736, filed Sep. 9, 2018; application Ser. No. 16/125,736 is a continuation of U.S. patent application Ser. No. 15/236,888, filed Aug. 15, 2016, now U.S. Pat. No. 10,071,177 issued Sep. 11, 2018; this application also claims the priority benefit of U.S. provisional patent application 62/729,326, filed Sep. 10, 2018; the entire contents of all of these applications are incorporated herein by reference.

BACKGROUND OF THE INVENTION

Field of the Invention

This invention is in the field of improved hospital and operating room designs and sterilization methods. This invention is also in the field of computer vision, and automated operating room sensor and management systems.

Description of the Related Art

According to the Centers for Disease Control, in the US, there are approximately 1.8 million cases of Hospital Acquired Infections per year, and about 300,000 Surgical Site Infections a year. These infections are primarily caused by microorganisms (microbes) such as *Staphylococcus aureus*, coagulase-negative staphylococci, *enterococcus* spp., *Escherichia coli, Pseudomonas aeruginosa, enterobacter* spp., *Klebsiella pneumoniae, candida* spp., and other microbes. These infections result in a high rate of death and morbidity, and as well as a considerable amount of expense, and thus constitute a major medical problem. This problem is compounded because increasingly, these microorganisms are antibiotic resistant.

As a result, there has been a significant amount of interest in finding methods to reduce the number of microbes present in clinical areas, such as hospital operating rooms, emergency rooms, rooms for immunocompromised patients, and other clinical areas.

Some workers have focused on methods of delivering clean air to such areas. This includes the methods of Panelli (U.S. Pat. No. 6,132,309), Beaver (U.S. Pat. No. 7,125,332) and Curstejee (US 2011/0097986). Additionally, modern practice in this area commonly includes the use of High-efficiency particulate arrestance (HEPA) filters, Ultra Violet (UV) sterilization techniques, and fixed airflow rates. Additionally, various regulatory codes and standards, such as requirements for a minimum number of air change rates per hour to maintain adequate ventilation, also are important in this area.

Other workers have focused on methods to provide vapors or other airborne disinfecting agents. Here Bioquell Inc., a UK company with US offices in Horsham Pa., has been active. Prior art by Bioquell includes Watling (U.S. Pat. No. 7,186,371), Martin (U.S. Pat. No. 7,674,440), and Pomeroy (US 2014/0037496). Other work in the field includes Shannon (U.S. Pat. No. 8,551,399).

Prior art patents and patent applications on intelligent systems and sensors for operating rooms includes the work of Abri, U.S. Pat. No. 8,452,615; Robbins, US patent publication 2014/0006943; Fireman, US patent publication 2009/0099862; McGreevy, U.S. Pat. No. 7,317,955; and Sanchez, U.S. Pat. No. 7,557,710; the entire contents of these applications are incorporated herein by reference. Prior art publications in this field include Agarwal et. al., "A Pervasive Computing System for the Operating Room of the Future", Mobile Networks and Applications, Volume 12 Issue 2-3, March 2007 Pages 215-228; and Bardham and Norskov, "A Context-aware Patient Safety System for the Operating Room", UbiComp '08, Sep. 21-24, 2008, Seoul, Korea.

Despite these and other efforts, the incidence of Hospital Acquired Infections and Surgical Site Infections remains unacceptably high. Thus, further advances in the field are needed.

BRIEF SUMMARY OF THE INVENTION

The invention, here occasionally designated in the alternative as the "Clean Cube", is based, in part, on the insight that microbes can exist on essentially each and every surface of a hospital or clinic treatment room (here these are often referred to as a "chamber"), including hidden or obstructed services, and that the only way to assure that the microbial burden is consistently reduced is to employ airborne sterilizing agents that can penetrate to all surfaces of the hospital or clinic room. Certain aspects of the invention were previously described in parent U.S. patent application Ser. No. 15/236,888, as a "Clean Cube"; the entire contents of this application are incorporated herein by reference.

The invention is also based, in part, on the insight that such airborne sterilizing agents are generally harmful to humans, and thus to be able to be used on a frequent basis, systems and methods must be devised to make the operation convenient, simple, safe, and nearly foolproof.

The invention is also based, in part, on the insight that even after an effective sterilizing cycle, microbes will again enter a room as soon as the room is opened to the outside, and humans again enter the room. Thus, to reduce the risk of microbial borne infections, it is useful to employ air curtains of sterilized air (often HEPA and/or UV sterilized air), often best delivered by various types of laminar flow delivery devices. These laminar flow delivery devices should ideally be configured in a manner that is compatible with the use of the previously discussed airborne sterilizing agents.

In some embodiments, the invention may be a system and method of reducing the risk of microbial infections such as Hospital Acquired Infections (HAI). This system and method will typically rely upon rooms (chambers) equipped with airborne sterilizing agent generators, suitable occupancy and environmental sensors, control mechanisms, and electronic actuator regulated air control devices so as to allow, with very little operator effort, the same chamber to be both thoroughly treated with airborne sterilizing agents, and afterwards also provide suitable laminar flow sources of sterilized air.

The present invention is also based, in part, on the insight that the previously described "Clean Cube" invention represents a uniquely suitable environment to implement an operating room (OR) and/or other clinical and critical space "intelligent platform". This intelligent platform can share a number of components and functions in common with the previously described Clean Cube. The intelligent platform embodiment of the Clean Cube can also be configured to perform additional sensing, monitoring, capturing and storing real-time data that can be used to further ensure the integrity of the clean environment at various times before, during, and after various surgical procedures. This additional intelligent platform functionality can also be used for other functions as well. These include automated acquisition of clinical information, interaction with other available subject matter experts, and to provide feedback to the surgical team and facilities managers before, during and after surgery.

Such concepts were previously discussed in U.S. provisional application 62/729,326, the entire contents of which are incorporated herein by reference. There, the intelligent platform aspects of the invention were occasionally designated as "Operating Room Information Capture and Knowledge" (ORICK) systems and methods, and this terminology will be occasionally used in this disclosure as well.

The present invention is also based, in part, on the insight that although, to reduce the rate of HAI, it is important to keep track of personnel and materials entering and exiting the chamber, many times such personal and materials entering and exiting the chamber will not be adequately labeled or adequately documented. Thus, methods of detecting non-documented and unlabeled personnel and materials can be particularly useful. Here the use of modern "artificial intelligent" computer vision systems can be particularly useful, because an adequately configured computer vision system can, in principle, automatically recognize and classify such non-documented and unlabeled personnel and materials. As a general rule of thumb, non-documented personnel and materials are associated with a higher risk than documented personnel and materials. Thus, in some embodiments, the invention can be configured to automatically correlate the personnel and materials recognized and observed by the computer vision system, with those personnel and materials documented by suitable identification means (optical codes, RFID tags). Computer vision recognized personnel and materials without matching identification, and other events as well, can then be automatically evaluated versus predetermined algorithms or "policies", and the system can be configured to automatically flag exceptions.

In addition to facilitating the operation and maintenance of the "Clean Cube", the intelligent platform or "ORICK" embodiment of the invention can also be used for various medical informatics purposes, such as providing access to a vast database of surgical, operating room, and/or other clinical and critical space data. The intelligent platform can be used to store as well as retrieve medical data as well. Thus, in some embodiments, the intelligent platform can be used for further analysis of operating room and/or other clinical and critical space techniques. The intelligent platform can be used to help manage scheduled events, logistics, and medical planning purposes. Towards these ends, the intelligent platform may use various artificial intelligence (e.g. CNN methods, to be described shortly) and 'Big Data' techniques and methods. The net result is that the intelligent platform aspects of the present invention can help produce continuous improvements to both the operating room environment and, help produce more successful surgery outcomes.

To further improve the intelligence of the previously described invention, without compromising the Clean Cube's primary function as a microbe-free site for surgery, additional sensors and monitors may be provided in the Clean Cube's chamber. Additionally, the system's processors may be further upgraded with additional software and analytic/metrics configured to collect, store, retrieve and display various types of data. The system's processors can also be further upgraded with additional software configured to provide real-time and archival information to various personnel associated with the facilities, the surgeries, the training, the Clean Cube operating room/chamber, and/or other clinical and critical space and equipment designs.

An important objective of the improved intelligent platform methods described herein is to provide more useful and successful outcomes measurements and follow-ups, as composed to the prior art (e.g. today's standard of care, hospital administration and business modeling/developers). In particular, an important objective is to provide an intelligent platform that enables improved learning from real data and facts recorded during thousands of various (e.g. like and dissimilar) operating room or other clinical and critical space activities. The net result would be to enable improved results and lower costs of medical care.

BRIEF DESCRIPTION OF THE DRAWINGS

FIG. 9A shows a long axis side view of an individual laminar air flow system module. Here more details of the air supply connection and damper and the LED drivers (used to power the system's Light Emitting Diodes) may be seen.

FIG. 9B shows a view looking up at the face of an individual air flow system module. Here details of the perforated wall structure and LED lighting may be seen.

FIG. 9C shows a short axis side view of an individual laminar air flow system module. This shows a detail of the air supply connection and damper from a different perspective.

FIG. 11A shows an example of how the chamber's video cameras and computer vision system can recognize the presence and locations of various humans, such as the patient and various personnel, in the chamber as a function of time.

FIG. 11B shows an example of how, by storing a record of the position and location of various identified and unidentified humans and objects as a function of time, certain operating room "exceptions" can be automatically detected and flagged by the system.

DETAILED DESCRIPTION OF THE INVENTION

Nomenclature

Figure 1:
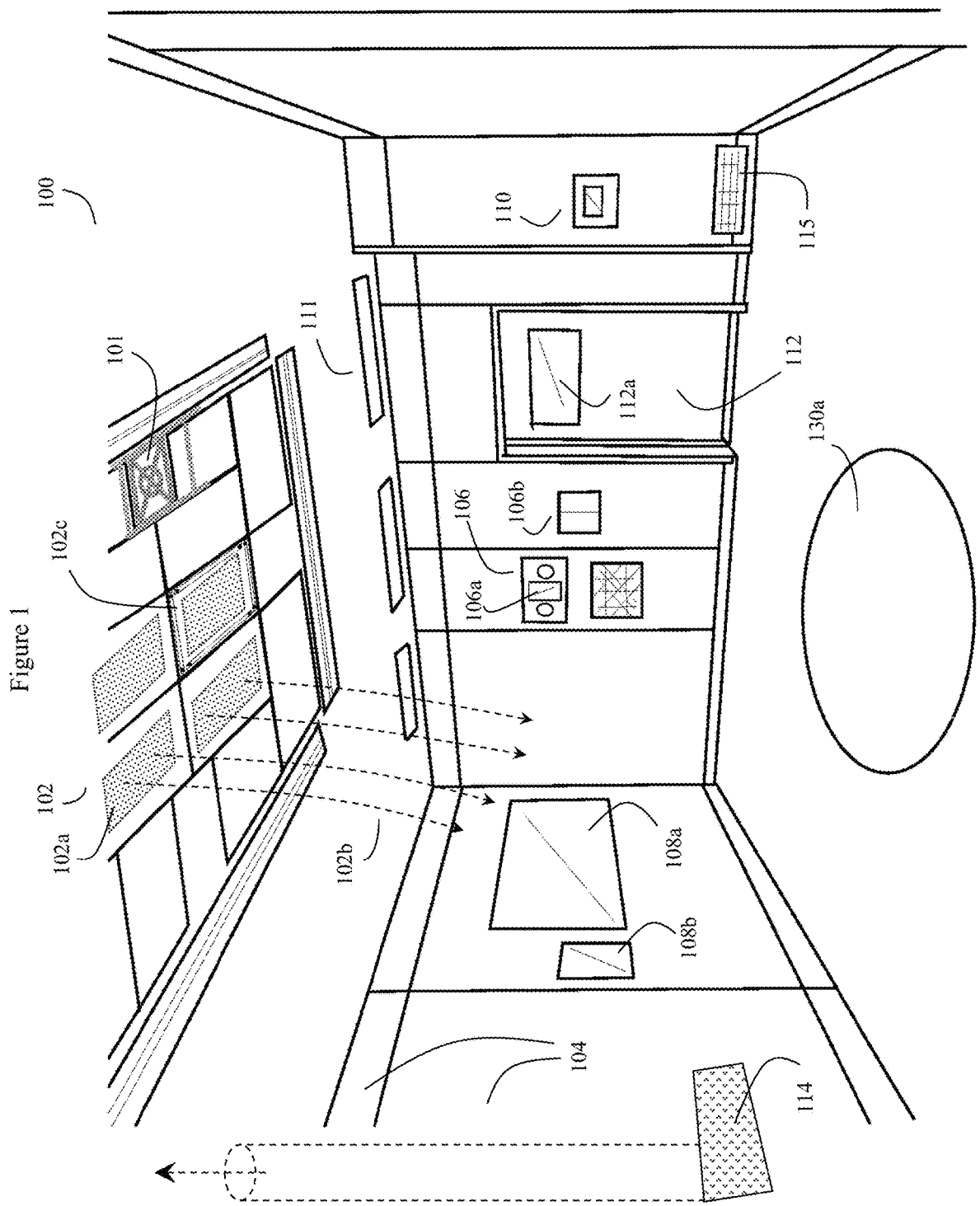
FIG. 1 shows an example of an operating room type chamber configured according to certain embodiments of the invention.

In this disclosure, the term "chamber" will often be used as a generic term for the room where the invention's systems and methods are being applied. Although hospital or clinic operating rooms are often used as specific examples for this type of room, these examples are not intended to be limiting. For example, the invention's systems and methods may also be applied to non-operating room hospital or clinic rooms, such as Intensive Care Units (ICU), NICU, PICU, pharma and medical device assembly areas requiring ascetic/sterile environments, and may be particularly useful where immunocompromised or infectious patients may be treated. The invention may also be useful for mobile clinics, field hospitals, combat support hospitals, and the like.

In this disclosure, the term "microbial" or "microbe" will be used to discuss bacteria, fungi, spores, viruses, and other microscopic pathogens, in particular, microscopic pathogens associated with Hospital Acquired Infections (HAI) and Surgical Site Infections (SSI).

In this disclosure, the term "HAI" will be used as a generic term to discuss infections obtained from these microbial pathogens in a hospital or clinic setting, and SSI are considered to be a subset of HAI. Thus, the term "HAI" encompasses "SSI".

In this disclosure, "damper" will often be used as a term for a valve or plate used to regulate the flow of air inside of a duct or other type of air handling device. Here unless otherwise specified, assume that the dampers are equipped with solenoids, motors, or other actuator mechanisms that allow the dampers to be opened or shut by a control mechanism, which may be a computerized control mechanism. Note that the term "valve" and "damper" are often used as alternate expressions for the same thing.

Use of computer-actuated dampers, sensors, and other computer automated methods: A large percentage of clinic and hospital unfavorable events are caused by human error. Thus, in a preferred embodiment of the invention, many of the devices and methods described herein may be computer-controlled methods, used to reduce such human error related problems. However, unless explicitly claimed, use of computer control methods are not intended to be limiting. For example, in some embodiments, it may be necessary to operate the system in a fallback method under direct human control. In other embodiments, it may be useful to include the option of direct human control over certain equipment to allow for human supervision and interruption of certain sequences when, in the judgment of the human operators, such direct human control is necessary.

In some embodiments, the invention may be a hospital or clinic chamber-based system and method of reducing a risk of HAI. In a preferred embodiment, this will be an automated system and method that is controlled by one or more computer processors. This chamber will typically have a supply air (e.g. a damper-controlled outside air) intake that will take outside air and sterilize it (often by using a HEPA filter and/or UV sterilizer), as well as a damper-controlled air return. In some embodiments, the chamber may distribute this sterilized outside air inside the chamber by using an optional ceiling-mounted structural device (e.g. a load bearing structure, and a laminar air flow system (e.g. laminar array) mounted on the structural device), to blow HEPA filtered and UV (or other method, such as hydroxyl generator methods) sterilized supply air over a defined field in the chamber, thus providing an air curtain that helps protect against airborne microbes.

Note that although the optional ceiling-mounted structural device performs multiple purposes, such as supporting the laminar array, providing support for hanging medical equipment, and other functions, typically the HEPA filters used to provide HEPA treated air will reside elsewhere, and the HEPA treated air will flow to the laminar array mounted on the ceiling mounted structural device through one or more air ducts, as is shown in FIGS. 3-6.

To sterilize the chamber, the invention will typically verify (often using computer vision and ORICK methods, to be discussed later in this disclosure) that no humans are present the chamber and then restrict access to the chamber. The invention will then typically isolate the interior air flow in the chamber from outside air (e.g. the hospital or clinic's main air supply) by closing at least one air return damper and at least one supply air damper. The invention will then typically activate an air phase anti-microbial agent generator, configured to fill the chamber with air phase anti-microbial agents at a time and dose level configured to kill at least a substantial majority of microbes in the chamber. Upon completion of this process, the invention will typically deactivate the generator, and set the dampers (e.g. at least opening the return damper and at least one supply damper) and other air flow mechanisms to flush the remaining air phase anti-microbial agents from the chamber, often using a catalytic converter to deactivate any remaining air phase anti-microbial agents. In other embodiments, particularly when air duct access to the outside of the building is available, the air phase anti-microbial agents can be rapidly purged to the outside air. This latter option is particularly useful for emergency purge situations, and/or when a rapid stop of the sterilization process mid-cycle is desired.

Information platform (ORICK) systems and methods:

In this disclosure, the information platform or "ORICK" embodiment of the invention supplements the chamber previously described in the parent application Ser. No. 15/236,888 (now U.S. Pat. No. 10,071,177) with additional sensors and additional computational capability. In particular, the ORICK embodiment of the invention will now typically comprise additional video sensors (e.g. video cameras), additional computer memory, and computer vision capable computer processors. The system may also be configured to receive and process information from operating room equipment and devices, such as surgical bed positions, surgical robot operational parameters, various medical sensors, and the like. In addition to video camera type sensors, other types of sensors, such as RFID detectors, Internet of Things (IoT) wireless gateways (often Wi-Fi transceivers), and various environmental sensors will also be added. The upgraded computer system will often be further equipped with more sophisticated software functionality (to be described), and will often be configured to interface with outside computer systems such as outside medical databases, facilities networks, and the like.

As will be discussed in more detail, the "ORICK" intelligent platform can be configured to continuously gather data on the movement of personnel and equipment in the chamber on a continual basis, both during cleaning and maintenance cycles, as well as when the chamber is being used as an operating room or (other healthcare chamber) by medical personnel. Additionally, the chamber can be configured to continuously analyze this data versus various algorithms (often called facilities policies), and automatically trigger alerts (e.g. "exceptions) when the ORICK system detects potential problems. As will be discussed, this can result in at least three types of benefits. An "ORICK" equipped chamber can optimize cleaning cycles and methods to achieve higher levels of sterility. Additionally, an "ORICK" equipped chamber can also monitor the movement of personnel and equipment during medical procedures, and also trigger exceptions when the data, as analyzed versus various algorithms or facility policies, suggests that a potential problem may be occurring. A third benefit is that the same sensors and high capability computing equipment used to perform the previously described functions can also be used for various maintenance and medical informatics applications, as will be described.

The present invention can thus be viewed as being a combination of an ORICK-like intelligent platform, combined with at least a simplified version of the healthcare chamber described below. Here in the first part of the specification, we will first describe various embodiments of the healthcare chamber itself. In the second part of the specification, we will then describe the intelligent platform that integrates with the chamber, and describe how the various components can work together to provide improved healthcare outcomes.

Turning to the chamber component of the invention: In some embodiments, the chamber component of the invention may be a system or method of reducing the risk of HAI (e.g. by reducing the microbial burden of a room used in patient care). This method relies, in part, on a combination of airborne antimicrobial agents to find and inactivate microbes on various surfaces and items in the room, and laminar airflow systems configured to use air curtains of sterilized air to help direct microbes away from patients.

Expressing the chamber component of the invention in methods terminology, the chamber component of the invention may comprise various devices and various steps, all working together as a system. To reduce the microbial burden of the room or chamber, the invention operates by verifying (often by automatic devices, such as the ORICK computer vision system, to be discussed) that no humans are present in the chamber and then (again often by automatic devices) restricting access to this chamber prior to the commencement of sterilization.

Note that the chamber will preferably comprise air impermeable chamber walls, ceiling, and floor, although in some cases, walls or ceilings with limited porosity may also work so long as the porosity is limited enough as to constrain sterilizing agents inside the chamber, and to constrain the migration of microbes outside the chamber from migrating through the walls to inside the chamber. The walls of the chamber will typically be made of a material that is easy to clean, and that is not adversely affected by the sterilizing agents. Here materials such as glass and stainless steel, or other material able to withstand degradation by the sterilizing agent may be used.

Chambers intended for human occupancy typically provide air flow by providing a system by which outside air can enter into the chamber, and interior air inside the chamber can return to the outside air. Often this air flow is controlled by appropriate dampers. Here, the invention will typically operate by isolating (often by automatic devices), the interior air flow in the chamber from outside air by closing at least one return damper (typically actuator controlled) and at least one supply air damper (also typically actuator controlled).

For some clinical chambers, such as operating rooms, it is desirable to configure the chamber air supply so that the chamber obtains interior air from sterilized outside air. According to the invention, this sterilized outside air may be distributed inside the chamber using a laminar array (laminar air flow system) mounted or associated with a ceiling mounted structural device. This laminar array portion of the ceiling mounted structural device will typically comprise a load bearing structure, with a laminar air flow system mounted on the structural device. This laminar air flow system may be configured to blow sterile air (typically HEPA filtered and UV (or hydroxyl generator sterilized supply air) over at least a defined field in the chamber, often forming an air curtain around this defined field. For an operating room, this defined field may be the operating table. To control the supply of sterile outside air, in some embodiments this laminar air flow system will be connected to at least one supply air damper (preferably also actuator controlled and often configured for automated operation).

For the sterilization cycle, the invention may operate by closing (often by automatic devices) at least one (actuator controlled) supply air damper, and activating (often by automatic devices) an air phase anti-microbial agent generator. This generator will typically be configured to fill the chamber with air phase anti-microbial agents, such as a hydrogen peroxide vapor or mist, and to keep the levels of these agents elevated for a time and dose level configured to kill at least a substantial majority of the chamber's microbes. The invention may also monitor the environment inside the chamber, and adjust other parameters, such as temperature and humidity, so that the sterilizing agent acts in a consistent and predictable manner.

Following this microbial reduction cycle, the invention will then typically (often by automatic devices) deactivate (e.g. turn off) the generator, and flush (again often by automatic devices) any remaining air phase anti-microbial agents from the chamber by, for example, at least opening the (actuator controlled) return damper and opening at least one (actuator controlled) supply damper. Fans may also be activated as appropriate. This acts to flush the air phase antimicrobial agents from the chamber.

When viewed from the operating room standpoint, the net result is to obtain an operating room with an unusually low microbial burden, and configured, even after the sterilization cycle, to keep the microbial burden low over at least certain defined fields or regions of the chamber (e.g. over the operating table) by providing laminar flow sources of sterile air that, for example, may provide an air curtain against any airborne microbes carried by dust particles or droplets entering these regions or fields.

Figure 2:
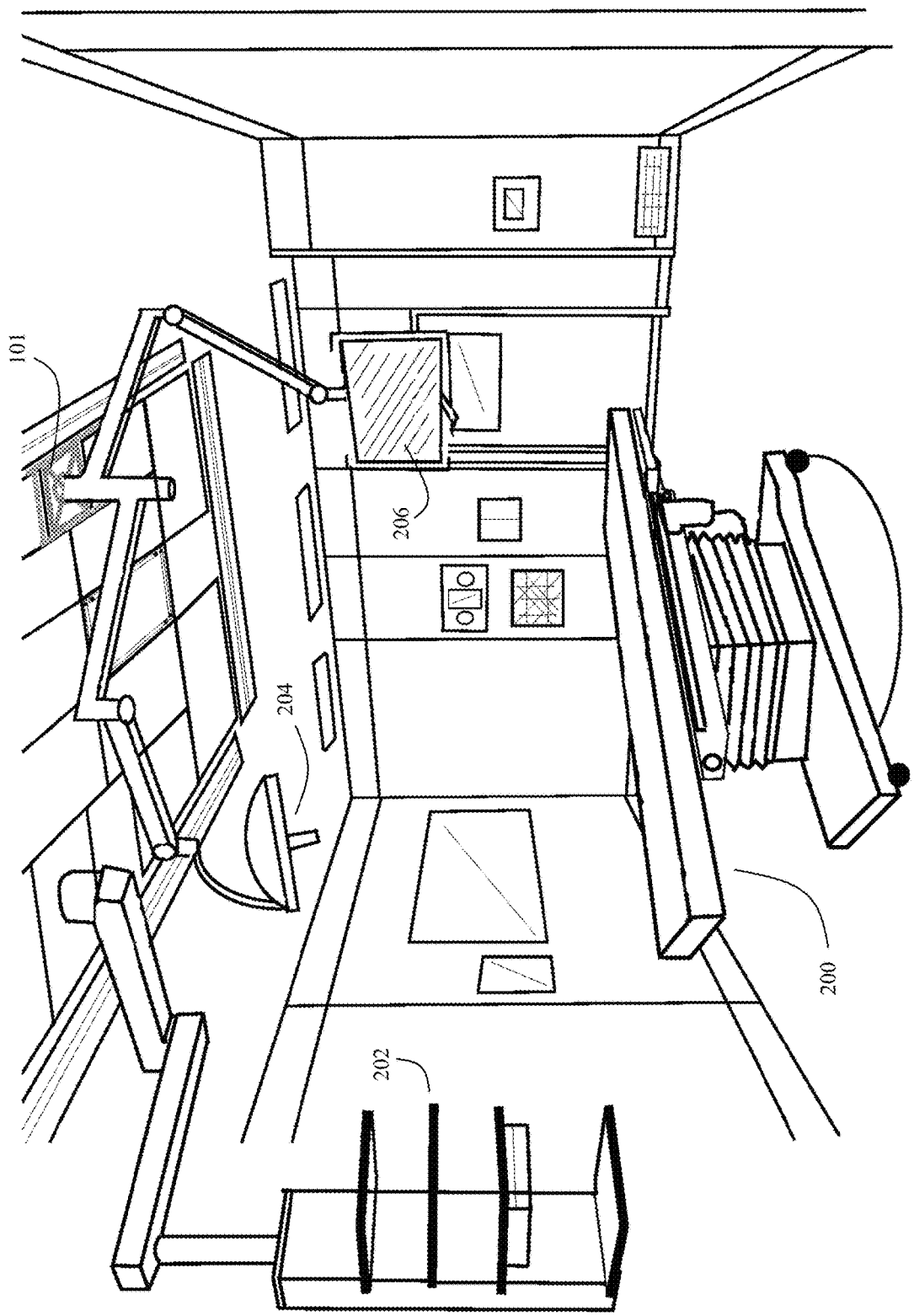
FIG. 2 shows an embodiment of the operating room or chamber configured with an operating table and various types of boom mounted operating room equipment.

FIGS. 1 and 2 show an example of such an operating room type chamber (100) configured according to certain embodiments of the invention. On the ceiling, the invention's ceiling mounted structural device (101) can be mounted. In addition to accommodating an array of laminar air flow devices and other utilities such as lighting, this structural device (101) can support a modular grid system with a load bearing structure configured to accommodate multiple types of ceiling mounted devices with various weights (loads) and dimensional tolerances. This structural device (modular structural grid) (101) may thus support the ceiling (e.g. provide an apparent ceiling to inside observers), the laminar array, medical equipment, as well as access to various hospital or clinic utilities (e.g. power, medical gas, etc.) as desired.

Figure 7A:
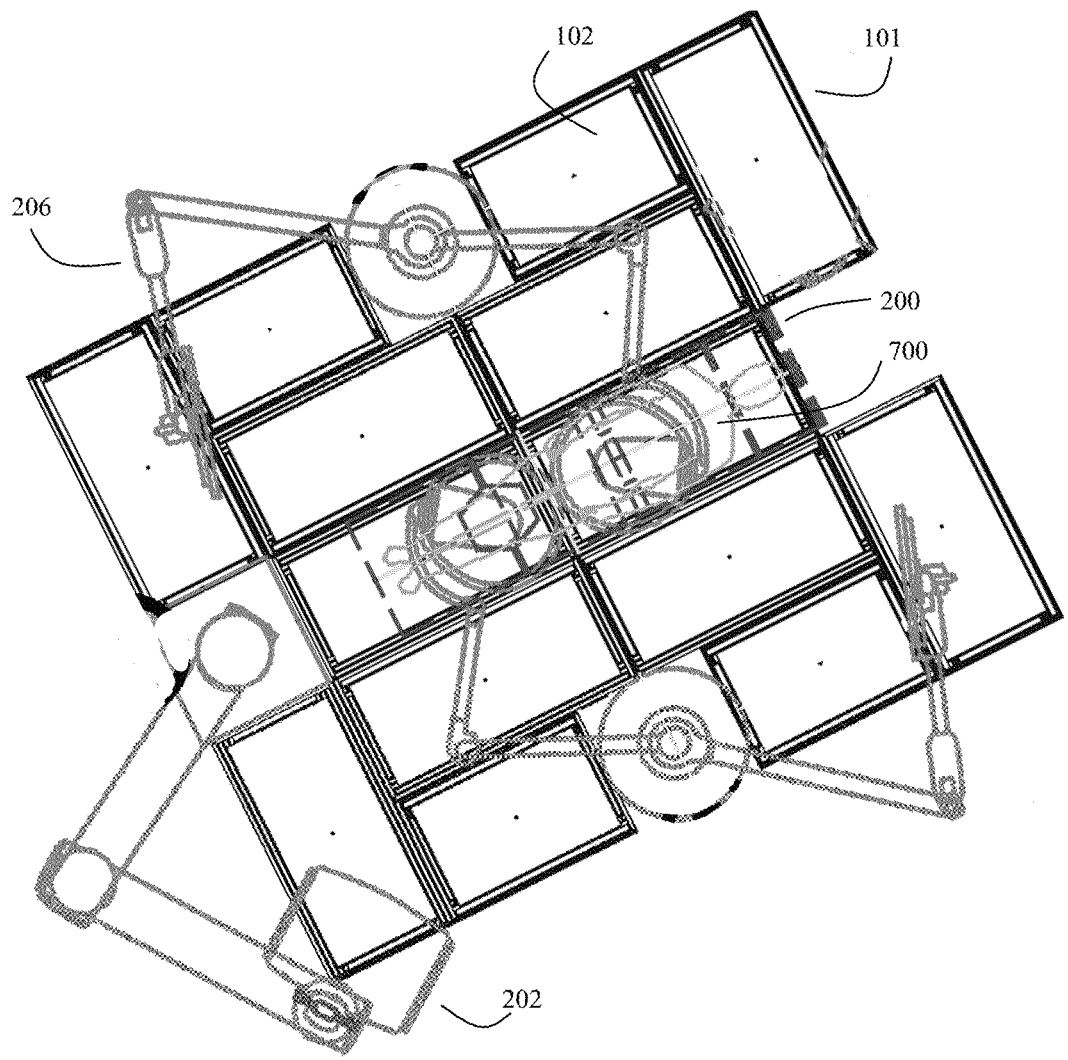
FIG. 7A shows a top-down view of a portion of an operating room type chamber as seen from the perspective of a viewer positioned above the invention's ceiling mounted structural device.
Figure 7B:
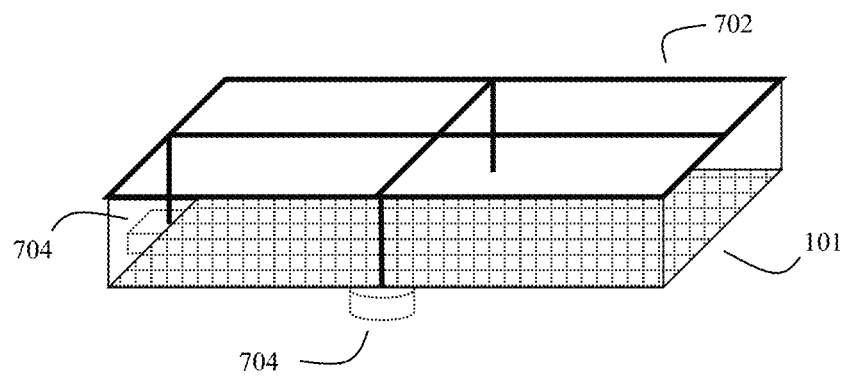
FIG. 7B shows a detail of how the ceiling mounted structural device may be mounted in the ceiling of an operating room.

In some embodiments, it may be useful to use a prefabricated structural system, such as a system of powder coated structural steel grids, to form a plurality of internal grids configured to provide underlying support for the array of laminar flow devices, medical equipment, and utilities held by structural device (101), see also FIG. 7B (702).

In some embodiments, which may be particularly useful when the chamber is an operating room and the defined field in the chamber is an operating table, the ceiling mounted structural device may have a generally polygonal shape, such as a rectangular shape, or a more complex shape formed from a plurality of rectangles. This ceiling mounted structural device may be further configured with a plurality of internal grids. In a preferred embodiment, at least some of these grids may be configured to accommodate electrical conduits, preferably larger conduits with diameters of around 2 inches for maximum compatibility with a broad range of additional equipment, such as equipment useful for Operating Room (OR) purposes. At least some of these grids or other grids may be configured to supply structural support for additional equipment, such as for standard operating room utility pendants/booms, surgical lights, and other boom-mounted equipment. This is shown in more detail in FIG. 2. See also FIGS. 7A-8B.

The ceiling mounted structural device (101) will also typically have various mounted laminar air flow systems (102), which will introduce clean HEPA filtered (and often UV sterilized) supply air into the operating room, often through perforations in the overhead lighting fixtures (102a) (perforated panels). This laminar air flow system (102) will often be designed so as to produce a perimeter air curtain (102b) over a defined field of the operating room, such as in the region (130a) where an operating table may be placed. Here the lighting system may incorporate integrated lighting, such as integrated light emitting diode (LED) lighting. This lighting may be disposed in a perimeter (102c) around the perforated panels (102a), or in other locations.

Put alternatively, this laminar air flow system may, in a preferred embodiment, further comprise a plurality of air curtains that produce a plurality of directionally-controlled airstreams (102b). This is often referred to in the alternative as a "laminar array". These airstreams are configured to reduce penetration of particles from area outside of the operating table to an area inside the operating table.

As previously discussed, the walls of the chamber (104) will often comprise materials selected to be easy to clean and sterilize, and resistant to any deterioration caused by air-phase anti-microbial agents such as hydrogen peroxide ($H_2O_2$). These materials can comprise medical grade glass (or glass-like material), stainless steel, or other easy to clean materials that are resistant to deterioration caused by the airborne sterilizing agent(s).

The walls (104) may or may not have illumination or customized backgrounds. In some embodiments, it may even be useful to put computer-controlled display screens behind transparent walls so that the appearance of the operating room can be customized according to the needs at hand. The wall displays may, for example, be configured to a pleasant and reassuring display to show patients upon entry. The wall displays can then be reconfigured during an operation, as desired, to show images containing medical information, thus making it easy for physicians to request additional data in an easy to see format as desired.

In some embodiments, at least the substantial majority (e.g. greater than 50% and often greater than 90%) of the chamber's walls may be covered with materials, such as glass or stainless steel, selected to be resistant to the particular air phase anti-microbial agents that are being used.

The system will also comprise an air phase antimicrobial agent generator (106), such as a hydrogen peroxide vaporizer/fogger/aerosol generating unit shown here as a particular example.

This generator may operate according to methods of Pomeroy (US 2014/0037496), Watling (U.S. Pat. No. 7,186,371), Shannon (U.S. Pat. No. 8,551,399) or other methods. This generator (106) may further comprise a control touchscreen (106a), such as a hydrogen peroxide fogging control touchscreen, and containers of the antimicrobial agent (106b), such as modules configured to hold bottles of hydrogen peroxide.

In some embodiments, the generator may operate by converting an aqueous solution of hydrogen peroxide into air phase hydrogen peroxide by using any of a misting, nebulizer based, vaporizing based, or aerosol generating type process.

Some air-phase antimicrobial agents, such as hydrogen peroxide, require that the room humidity and/or temperature be controlled in order to achieve maximum anti-microbial effectiveness. Thus, in some embodiments, the air phase anti-microbial agent generator may be a combination generator and humidifier that also operates by regulating humidity, or alternatively the chamber may contain humidity and/or temperature sensors and regulating equipment that operates independently of the generator.

In some embodiments, the system will also comprise one or more medical grade touch-workstations (108a, 108b) for medical information, medical images, and other digital media. This workstation may optionally be integrated into the glass walls (104) of the chamber for greater sterility and to protect the workstation electronics. Other touch panels may also be provided for other functions, such as controlling other room lighting (111).

In a preferred embodiment, the invention will further comprise at least one computer processor, which will be configured to control many or all of the invention's various steps. In these embodiments, for example, this (at least one) computer processor may be used (often in conjunction with various occupancy sensors). Prior to the start of a sterilization cycle, this computer processor may use the occupancy sensors to first verify that no humans are present in the chamber and then to restrict access to the chamber (e.g. by automatically locking doors) so that outsiders cannot accidentally enter. Various safety overrides can, of course, also be incorporated into the system.

In some embodiments, this at least one computer processor may also be used to isolate interior air flow in the chamber from outside air by closing at least one computer controlled return damper and at least one computer controlled supply air damper (here assume that the chamber is configured to return interior air from inside the chamber to the outside using this at least one computer controlled return air damper). See FIG. 4 for more detail.

In some embodiments, the laminar air flow system may also be connected to at least one computer-controlled supply air damper, and the system's (at least one computer processor) may be used to activate the air phase anti-microbial agent generator (106).

In these embodiments, at the end of a sterilizing cycle, the system's (at least one) computer processor may also be used to deactivate this anti-microbial agent generator (106), and to flush any remaining air phase anti-microbial agents from the chamber by opening the computer controlled return damper and the (at least one) computer controlled supply damper. These steps are shown in more detail in FIGS. 3-6.

In some embodiments, this (at least one) computer processor may be controlled and monitored by using at least one touch panel equipped graphical user interface terminal. This terminal may be mounted either on an interior chamber wall (110) or exterior to the chamber, or in both places.

FIG. 1 shows an example of this type of computer processor control unit (110), which optionally may also be integrated or embedded into or behind the glass walls (104) of the chamber. These control units will often include a master system control-touch panel. This can be used for controlling at least portions of the sterilization process, sterilization safety systems (e.g. door locks, sensors), and the like. This or an alternative control panel may also be used to control other aspects of the chamber's environment, such as lighting, air conditioning, and the like. To prevent accidental misuse, it may be preferable to separate the sterilization control panel from the control panel used to implement more standard aspects of the chamber, such as lighting.

The chamber (100) will also typically comprise at least one door (112) or door system. This door system will typically be configured to hermetically seal when shut, and also will be configured with locks, such as computer-controlled locks. For safety purposes, these computer-controlled locks will usually have a manual override. For safety purposes, the door will also usually have one or more windows (112*a*) so that outside observers can visually confirm the occupancy status of the room. If exterior sterilization control panels are used, it may be desirable to locate these control panels so that anyone using the control panel can look through a window and see what is happening. Alternatively, an outside control panel can also incorporate video displays of the inside of the chamber. Again, the idea is to make sure that no one is present in the chamber before sterilization begins.

In a preferred embodiment, the chamber (100) will be equipped with at least one-way computer operated door locks. Here, using at least one computer processor to restrict access to the chamber can (for example) comprise setting these at least one-way computer door locks to restrict humans outside the chamber from entering into the chamber. For safety reasons, it would be useful to configure the locks so that any humans inadvertently left inside the chamber can manually exit even after sterilization starts. It may also be useful to configure the doors with manual "open" overrides on the outside as well.

Other methods of ensuring that no humans are present in the chamber (100) during a sterilization cycle can also be used. For example, at least one computer processor can be used to monitor at least one occupancy sensor (see FIG. 4, 400), and preferably a plurality of different occupancy sensors, to reduce the chances of error. These occupancy sensors may include one or more motion sensors, infrared sensors, video cameras, carbon dioxide sensors, sound sensors, and the like.

Figure 5:
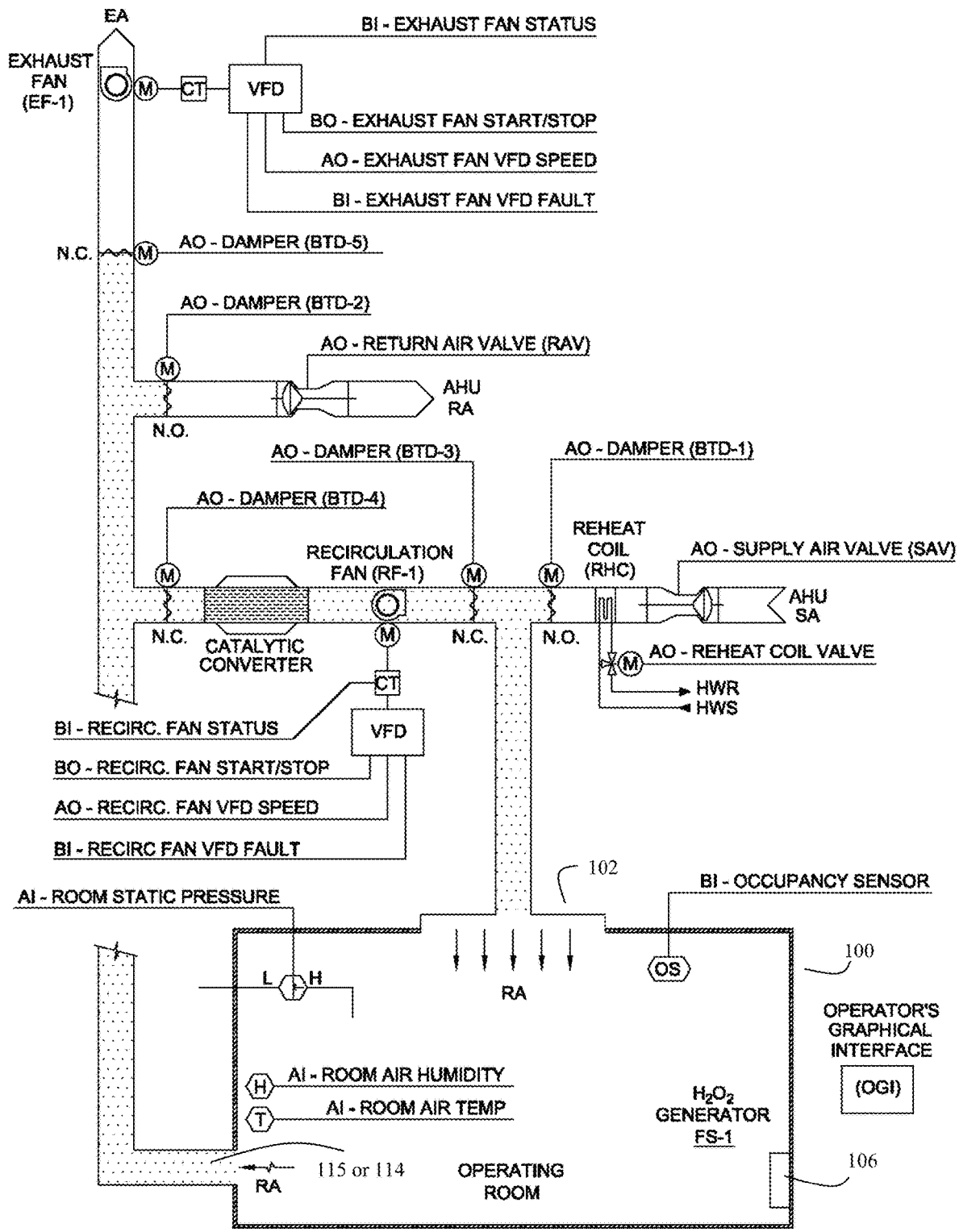
FIG. 5 how the invention may operate during a normal termination of a sterilization cycle.
Figure 6:
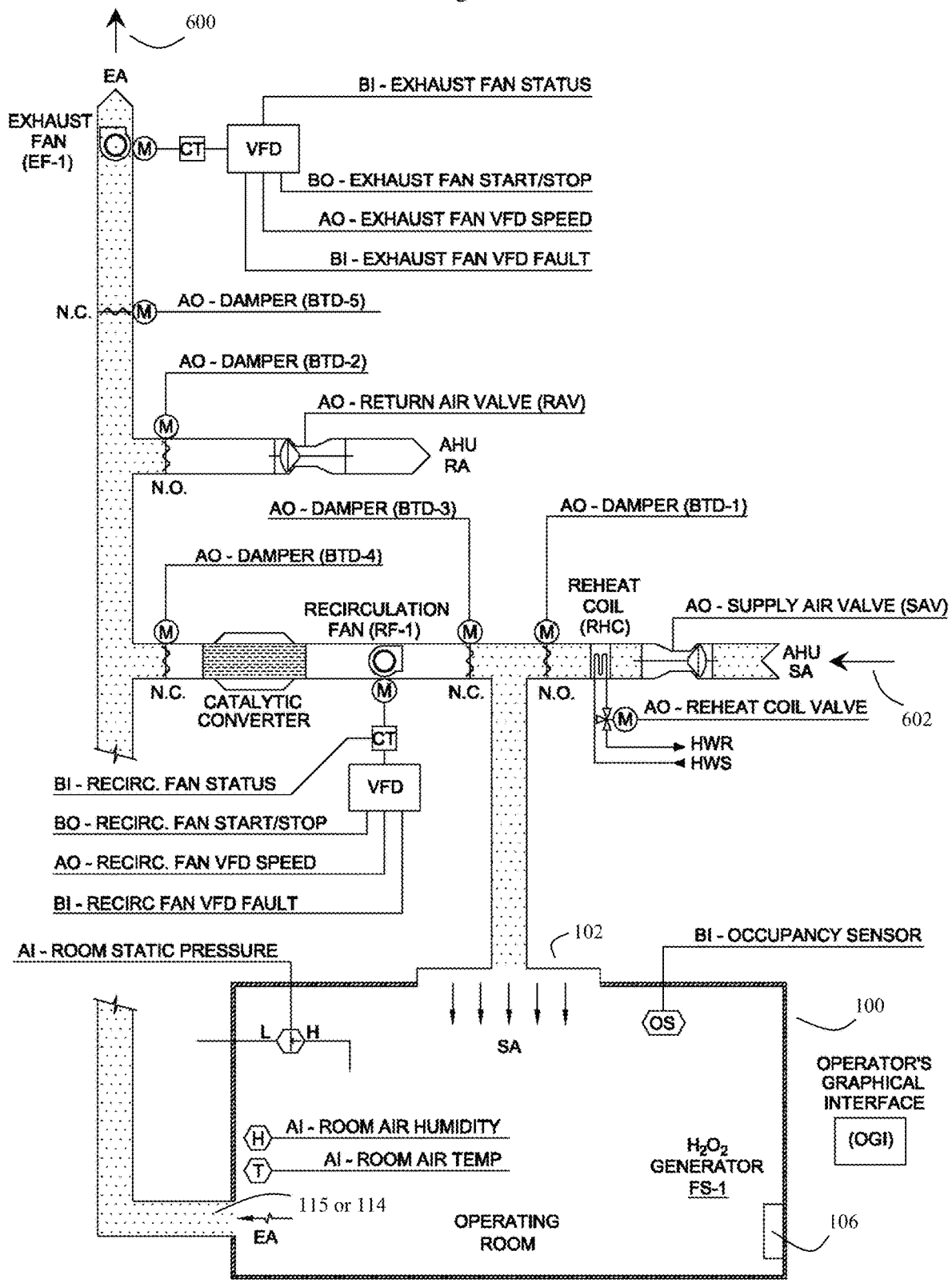
FIG. 6 how the invention may operate during an accelerated or "emergency purge" termination of a sterilization cycle.

After the sterilization cycle has commenced, before the chamber/room can be occupied again, residual air phase antimicrobial agents must be removed from the chamber (100). Here there are at least two ways to do this. One way, illustrated by FIG. 5, is to run the air though a built-in catalytic extraction unit that destroys all remaining antimicrobial agents. An alternative way, illustrated by FIG. 6, is to exhaust the antimicrobial agents into the outside atmosphere. These options can be selected based on available facilities and time available to complete the sterilization cycle. The rapid exhaust option can also be utilized if an emergency purge is required, and thus is sometimes referred to in the alternative as the "emergency" option.

As shown in more detail in FIG. 5, to remove air phase antimicrobial agents after the sterilization cycle, the chamber will also typically comprise a catalytic extraction unit comprising a room air intake, at least one fan, at least one a computer-controlled catalyst damper, and a catalyst (catalytic converter) to deactivate any remaining air-phase antimicrobial units. The air intake to this catalytic extraction unit is shown as (114). In some embodiments, this catalytic extraction unit can also be used as an emergency purge loop while in other embodiments (see FIG. 6), during emergency operation, for higher exhaust rates, the catalytic portions may be temporarily bypassed.

In the catalytic removal cycle, as shown in FIG. 5, the system may use at least one computer processor to turn on at least one fan to further flush remaining air phase antimicrobial agents from the chamber. The system may additionally, or alternatively, use at least one computer-controlled catalyst damper and a catalyst (catalytic converter) to deactivate any remaining air-phase anti-microbial agents.

The catalyst will typically act to degrade the air phase anti-microbial agents into harmless molecules. For example, if the air-phase antimicrobial agents are hydrogen peroxide ($H_2O_2$), then the catalyst may degrade these agents into harmless molecules such as water ($H_2O$) and oxygen ($O_2$).

As previously discussed, in some embodiments, the chamber (100) may be further equipped with at least one anti-microbial agent sensor configured to monitor the levels, concentrations, or amounts of the air-phase anti-microbial agents present in the chamber air. In at least computer control versions of the invention, this at least one anti-microbial agent sensor can further be configured to transmit data to at least one processor used to control the system. In a preferred embodiment, this at least one processor may be configured to set at least one-way computer door locks and door (112) so that the door only allows humans to enter the chamber after the anti-microbial agent sensor(s) report that the air phase anti-microbial agents are at a non-toxic level.

During conventional operation when the chamber is not going through a sterilization process, a more conventional air return (115) may be used.

FIG. 2 shows an embodiment of operating room or chamber (100), here configured with an operating table (200) and various boom mounted operating room equipment e.g. (shelves 202, lights 204, monitor 206) mounted on booms that are supported by the ceiling mounted structural device (101).

Figure 3:
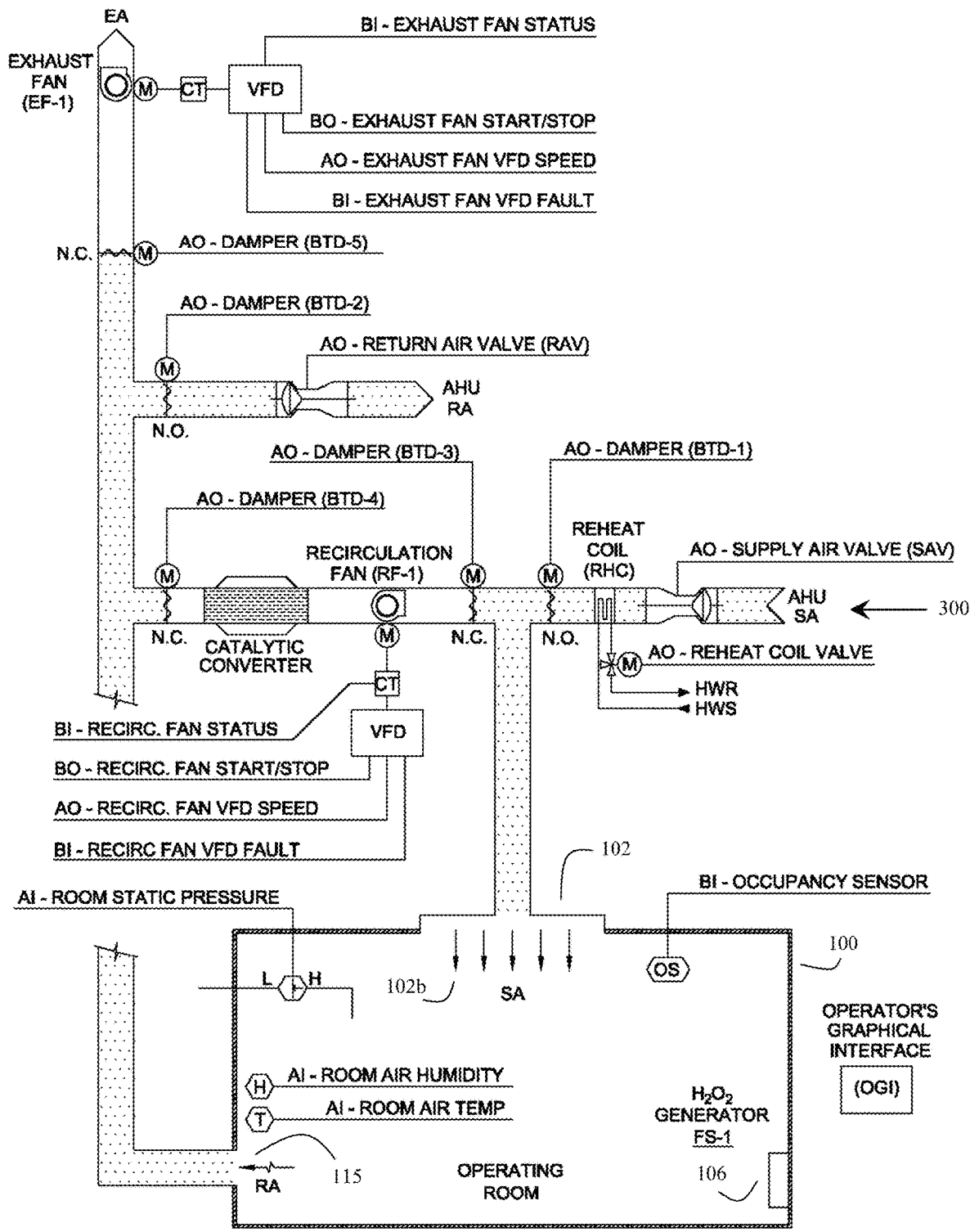
FIG. 3 shows how the invention may operate between cycles of sterilization.

FIG. 3 shows an embodiment showing how the invention's chamber sterilization equipment may act during normal operation, such as in between sterilization cycles, when the room may be occupied by physicians, patients, and other humans. Note that as previously discussed, the system may contain many computer connected and controlled air dampers (dampers), fans, and drivers that may, for example, be controlled by at least one computer processor. This at least one computer processor may form part of control unit (110), or may form part of another control unit as desired.

In FIGS. 3-6, the various terms are defined in Table 1 as follows:

TABLE 1

| Abbreviation | Meaning |
|---|---|
| AO | Analog Output (e.g. 0-10 volts) |
| AI | Analog Input (e.g. 0-10 volts) |
| BO | Binary Output (e.g. 24 volts) |
| BI | Binary Input (e.g. 24 volts) |
| BTD-X | Bubble Tight Tamper |
| EF-X | Exhaust Fan |
| N.O. | Normally Open |
| N.O. | Normally Closed |
| RF-X | Recirculation Fan |
| RHC | Reheat Coil |
| RA | Return Air |
| RAV | Return Air Valve |
| SA | Supply Air |
| SAV | Supply Air Valve |
| VFD | Variable Frequency Drive |
| SA | Supply Air |
| AHU | Air Handling Unit |

In normal operation, most of the system is shut down. Clean HEPA filtered air (300) enters through the supply air valve (SAV) in an open configuration, is optionally heated or reheated, and passes through normally open damper (air valve) BTD-1. (Here the term "bubble tight damper" or BTD denotes that the damper or air valve, when shut, closes tightly enough that when fluid is applied to test for sealing efficiencies, no bubbles can be found.)

The air passes through various optional HEPA filters and/or UV sterilizers (not shown) and will typically enter the chamber through the various mounted laminar air flow systems (102, 102a) previously shown in FIG. 1, and may form air curtains (102b) as desired. Return air exits the chamber via an air return, such as FIG. 1 (115). This return air is directed outside the chamber via normally open damper (air valve) BTD-2 and through the return air valve (RAV). This process may be assisted by various fans, as desired (not shown).

Figure 4:
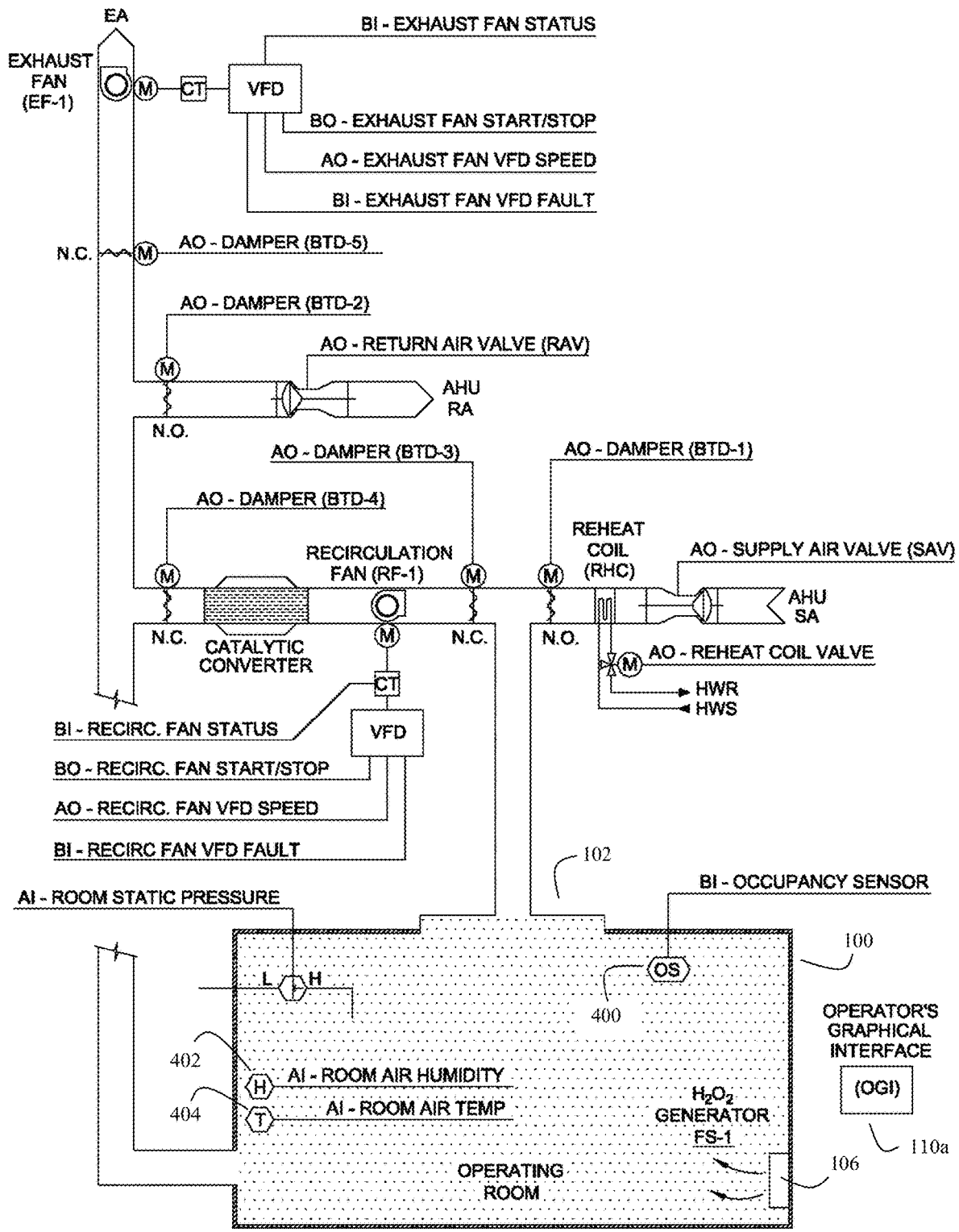
FIG. 4 shows how the invention may operate during the initiation of a sterilization cycle.

FIG. 4 shows an embodiment of how the system may operate during a sterilization cycle. As previously discussed, to ensure safety, before moving to this phase of the cycle, the system's computer processor will normally check the status of at least one occupancy sensor (400), and preferably a plurality of occupancy sensors operating by more than one detection modality, before initiating this sterilization cycle. This process may be controlled by suitable touch panel mounted graphical interface terminals mounted either inside the chamber (e.g. on an interior chamber wall, such as 110), or outside the chamber (e.g. 110a), or in both places.

Immediately before the sterilization phase, the computer processor, after verifying that the chamber (100) is empty, will then restrict access to the chamber by, for example, automatically locking door (112).

Often before the sterilization processes commences, the computer processor may monitor and adjust the room air humidity and temperature using appropriate sensors (402, 404), and optionally also monitor and adjust room static pressure as well, to optimize the integrity of the sterilization process.

During the sterilization phase, the computer directs normally open air valve (damper) BTD-1 to shut, and there is no air entering the room through the laminar flow system (102). The air phase anti-microbial agent generator (106) is turned on, flooding the chamber (100) with an air born sterilizing agents such as hydrogen peroxide vapor or mist. Normally open air valve or damper (BTD-2) is also computer directed to be shut, and normally closed dampers BTD-4 and BTD-5 are also directed to remain shut.

So, the sterilizing agent remains trapped in chamber (100), where it will sterilize the room and its various contents. During the sterilization process, in some embodiments, the computer processor may continue to monitor and adjust the room air humidity and temperature using appropriate sensors (402, 404), and optionally also monitor and adjust room static pressure as well, to help further ensure the integrity of the sterilization process. Other sensors may also be used to monitor levels of air-phase anti-microbial agents as well.

FIG. 5 shows how after sterilization, room (chamber) air may be exhausted through a catalytic system in order to remove any remaining sterilizing agent, and to once again make the room suitable for occupancy. The air phase antimicrobial agent generator (106) will be turned off, either by the system's computer processor, exhaustion of anti-microbial agents, or other method. The room air, which contains the air-phase antimicrobial agent, exits the room through the appropriate return air register (114 or 115). The computer closes normally open air valve (damper) BTD-2, and keeps normally closed air valve (dampers) BTD-5 and BTD-1 closed as well. The computer opens normally closed air valve (damper) BTD-4 and BTD-3, and turns on recirculation fan RF-1. As a result, air, containing the anti-microbial agents (e.g. hydrogen peroxide) passes through catalytic converter (500), where the antimicrobial agents are destroyed. The air, now free of any antimicrobial agents, reenters room (100) through the laminar air flow systems (102). This recirculation process can continue until the computer (usually assisted by various sensors and timers) determines that the level of remaining anti-microbial agents has now dropped to an acceptable level. Usually, the computer system will keep door (112) automatically locked until this time.

The one drawback of this catalytic recirculation method, however, is that it may take some time to operate. However this may change over time, as new and improved cleaning agents are developed, alleviating the dwell time period of the current fogger.

Additionally, today's OR environment is full of computer-controlled units that often have fans for cooling. These fans can provoke disruptions in the air currents and the clean air flows of the laminar air flow systems. The invention can provide an optional 'exhaust manifold' to capture this air and re-circulate it thru the invention's clean air system. Further, the recirculation system can embody its own continuously recirculating and air filtration elements to reduce airborne microbes and bioburden during and in between surgeries. In some embodiments, the operating room equipment and recirculation system can be interconnected to channel such exhaust air and greatly reduce any disruptions.

FIG. 6 shows an alternate Emergency purge/Rapid exhaust process method of quickly removing anti-microbial agents from chamber (100). Here, as before, the system turns off the air phase antimicrobial agent generator (106). However, the system bypasses the catalytic converter and recirculation system. Instead, the computer opens normally closed air valve (damper) BTD-5, and activates exhaust fan EF-1. The normally open damper BTD-2 is closed, and the normally closed damper BTD-4 continues to remain closed. Thus, the chamber air, with its anti-microbial agents, may be directed outside the building via EA (600).

During this Emergency purge/Rapid exhaust process, the system directs normally open air valve (damper) BTD-1 to remain open. Thus, clean HEPA filtered supply air (602) passes though the supply air valve (SAV), is optionally heated or reheated as desired, and this clean air, free of anti-microbial agents, enters the room through the laminar air flow systems (102).

An example of a sequence of operations, such as one that might be used by the system's at least one computer processor, and as also discussed in FIGS. 3-6, is shown below:

1.0 Standard (Surgery/Treatment) Operation:

All operations shall be controlled by an operating room specific controller and shall have full BacNet interface with the facilities Building Automation System (BAS). Each Operating Room (100) will have an Operator's Graphical Interface (OGI, 110, 110a). All set points and adjustments can be made at the OGI or at the facilities BAS.

A. Supply Air Valve (SAV) shall modulate in conjunction with Return Air Valve (RAV) to maintain a constant air flow of 25 Air Changes per Hour (ACH) and maintain the operating room at a positive pressure to surrounding spaces. The operating room shall be maintained at +0.05 inwg. Status of the HVAC system airflow and pressure relationships shall be fully integrated and indicated on the OGI.

B. Operating room space temperature shall be maintained+72 F (adjustable) by modulating the flow of heating water to a reheat coil.

C. Operating room space humidity will be maintained at 50% RH (adjustable) by regulating output of a localized humidifier. If humidity control is provided at the base building air handling unit, the OGI shall monitor and report the space humidity condition.

D. General space lighting will be provided by full dimmable LED lighting fully integrated to the OGI. Lighting shall be able to change color to indicate operational status of the operating room.

2.0 Room Sterilization Operation:

All operations shall be controlled by an operating room specific controller (e.g. computer processor) and shall optionally have full BacNet interface with a facilities Building Automation System (BAS). Each Operating Room will have an Operator's Graphical Interface (OGI) (e.g. 110, 110a). All set points and adjustments can be made at the OGI, Hydrogen Peroxide generator (106) or at the facilities BAS. (Note, BACnet is a communications protocol for building automation and control networks, and is now exemplified by ISO standard 16484-5.)

A. Room sterilization operation shall be initiated by a time of day command or from a manual operator's command from the OGI. Manual override of a time of day start will be made at the OGI prior to the start of sterilization sequence of operation.

B. Upon initialization of the sterilization sequence the room (100) shall be confirmed to be unoccupied by at least one local occupancy sensor (400) within the operation room. Upon verification of zero occupancy a countdown timer shall indicated the sterilization cycle is ready to begin. The OGI shall indicate the room is vacant of occupants and ready for sterilization.

C. Following confirmation of the unoccupied room the operating room doors (112) shall close and lock and the OGI shall indicate confirm the status of the doors. This status shall be confirmed by end switches on the door slides as well as the electro lock (door lock). Red LED lighting integral to the space shall be illuminated to indicate the room is not safe for inhabitants. Manual kill switches/Door releases shall be located adjacent to all points of egress within the room.

Upon activation of a Kill Switch/Door release the system will require an operator resent at the OGI.

D. Upon confirmation and indication of the operating room doors (112) being closed and locked, the operating room shall be isolated from the main building air handling units by closing bubble tight control dampers (BTD). The SAV and RAV shall close in conjunction with dampers BTD-1 and BTD-2. The heating water valve on the operating room reheat coil shall be closed and the humidifier shall cycle off for the duration of the sterilization sequence. The status off the dampers shall be indicated on the OGI.

E. Upon confirmation of room isolation from the building air handling units, the sequence shall pause for a minimum of 300 seconds (adjustable) to assure the room is air is calm and all directional movement and turbulence has ceased. The status of the operation shall be indicated on the OGI.

F. Following the suspension of air turbulence, the room sterilization system (106) shall activate the hydrogen peroxide generator. The hydrogen peroxide generator shall sterilize the room based upon the onboard control systems. All status changes and actions shall be monitored at the OGI and the building automation system.

G. The hydrogen peroxide agent shall remain in the room until such time the generators onboard controls determine the room saturation has been achieved and the agent is ready to be evacuated.

H. Upon completion of the sterilization and dwell time the bubble tight dampers BTD-1 and BTD-2 isolating the catalytic convertor shall open. Upon confirmation of the dampers being fully open recirculation fan RC-1 shall activate drawing the operating room air and sterilization agent through the catalytic convertor. RC-1 shall run for a minimum of 360 seconds (adjustable) or until the rooms internal sensor indicates no sterilization agent remaining within the operating room. If a catalytic device is not incorporated within the design BTD-4 shall open and an operating room exhaust fan EF-1 shall activate to exhaust the agent. Upon confirmation of EF-1 start, BTD-1 shall open and SAV shall return to its normal operating condition to provide make-up air for the evacuation process. The evacuation process shall continue until the onboard controls on the hydrogen peroxide generator indicate the room is free of the agent.

I. Upon completion of the sterilization process, RC-1 shall deactivate and BTD-3 and BTD-4 shall close. Upon confirmation of closure of BTD-3 and BTD-4, BTD-1 and BTD-2 shall open. Upon confirmation of the open status of BTD-1 and BTD-2, SAV and RAV shall resume standard operation. The heating water reheat coil and humidifier shall be reactivated and shall operate in sequence until the operating room returns to its original adjustable set points. All activity and status shall be controlled and indicated at the OGI.

J. Upon confirmation status of the operating conditions of SAV and RAV, the door interlock shall be released and the red sterilization light shall return to the normal operation conditions. OGI shall indicate the OR is safe for occupancy and is ready for use.

FIG. 7A shows a top down view of a portion of the operating room (100) as seen from the perspective a viewer positioned above the ceiling mounted structural device (101). In the drawing, the observer is looking past the various laminar air flow systems (102) as if they were transparent or semi-transparent. The observer is also looking past various types of boom mounted equipment (e.g. monitors 206, shelves 202, lamps, etc.) and onto the top of an operating table (200) with a patient (700).

In a preferred embodiment, the operating table will be aligned with the orientation of the ceiling mounted structural device (101) and the various laminar air flow systems (102) so as to create an air curtain (FIG. 1, 102b) that sweeps the operating field clear of potentially microbe containing airborne particles.

Note that in some embodiments, as shown in FIG. 7A, the exterior dimensions of the polygonal shape of the ceiling mounted structural device (101) may exceed the exterior dimensions of the operating table (200). In some embodiments, this polygonal shape may be a rectangular polygonal shape (or at least may be composed of a plurality of rectangular polygonal shapes). The various laminar flow devices on the ceiling mounted structural device may be configured to produce a plurality of air curtains that may, for example, extend on all sides of a perimeter of the rectangular polygonal shape.

Ideally the ceiling mounted structural device and its various laminar air flow devices (e.g. laminar array) may be configured so that this air curtain perimeter will exceed the exterior dimensions of the operating table (200). This configuration will help further isolate the operating table (200) and the patient (700) from microbes borne on airborne particles originating from outside of the operating table.

As shown in FIG. 1, and elsewhere such as FIGS. 7A, and 8A-9C, in some embodiments, this laminar air flow system may be disposed on one or more interior structures within the rectangular shape of the ceiling mounted structural device (101). These laminar air flow systems may introduce an air flow configured to flush airborne particles from the area of the operating table (200) to an area outside of the operating table.

As previously discussed, for ease of construction, and compatibility with different types of equipment, at least some of the internal grids in the ceiling mounted structural device may be configured to accommodate electrical conduits with widths of at least 2 inches. Further, at least some of the internal grids may comprise weigh supporting members, some of which may be further equipped with flanges or other mechanical supports configured to supply structural support for standard operating room boom mounted equipment. See FIG. 7B for more examples.

FIG. 7B shows a detail of how the ceiling mounted structural device (101) may be mounted in the room. Here the ceiling mounted structural device (101) may either be a "false ceiling" that is mounted to structural support on the "real ceiling", or alternatively the ceiling mounted structural device may be suspended using modular support framing (702) or other type framing to various types of building structural supports (not shown). This modular support framing (702) may also be used to provide mechanical support for heavy boom mounted equipment (704) such as (202, 204, 206 etc.). This type of heavy boom mounted equipment is shown in Table 2 below.

TABLE 2

Boom and Lighting mount size (inches), weights & moments

| Vendor name | Mounting plate | Soffit | Weight/Moment |
|---|---|---|---|
| Stryker/Berchtold | T 23.5 × 23.5 | 25.5 × 25.5 | 2000 lbs/8020 ft lbs |
|  | S 15 × 15 | 23 × 23 | 1000 lbs/4020 ft lbs |
| Skytron | 17.5 × 17.5 | 24 × 24 | 1028 lbs/5606 ft lbs |
| Maquet | 20 × 20 | 25.59 round | 891-959 lbs/5962 ft lbs |
| Steris | TB 28 × 28 | 24 × 24 | 1987/11341 |
|  | T L 28 × 28 | 24 × 24 | 1732/8262 |
| Modular | 21 × 21 | 23 round | 1000 lbs 4010 ft lbs |

Figure 8A:
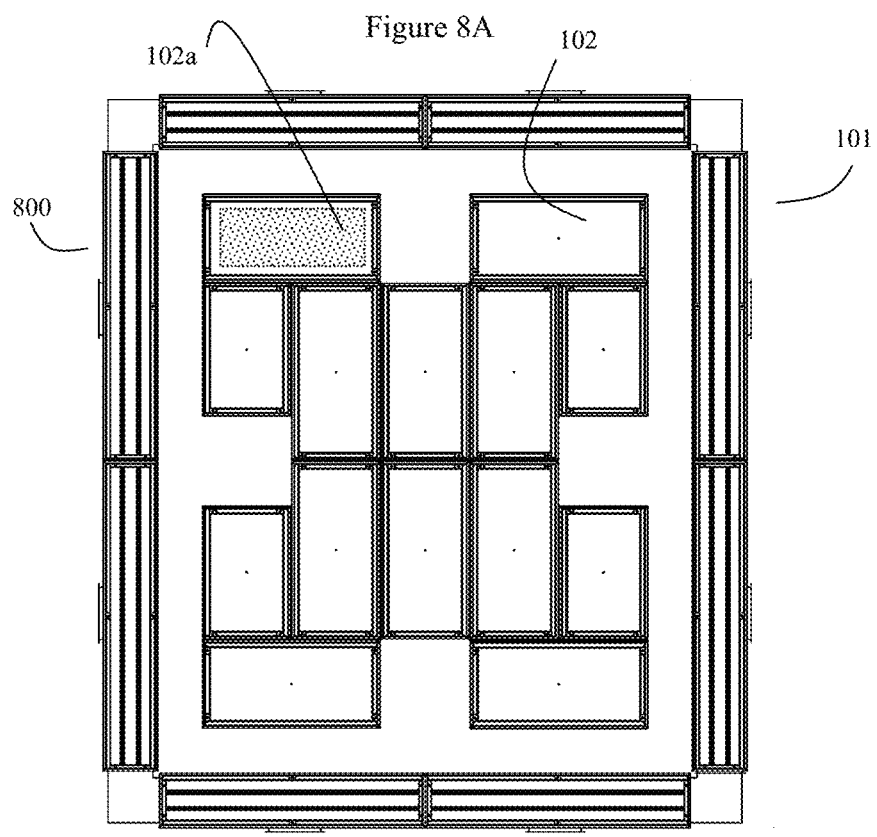
FIG. 8A shows an alternate view of the laminar array portion of the ceiling mounted structural device, here equipped with some additional perimeter lights and perimeter conduit paths.

FIG. 8A shows an alternate view of the laminar array portion mounted on the ceiling mounted structural device (101), here equipped with some additional perimeter lights (800) and perimeter conduit paths. Here assume that all of the mounted laminar air flow systems (102) are equipped with perforated panels (e.g. a perforated panel facing the room) (102a) so that air can flow gently into the room through a series of small openings (perforations). Examples of such perforated panels include the laminar flow diffusers produced by Krueger-HVAC, and other sources.

Figure 8B:
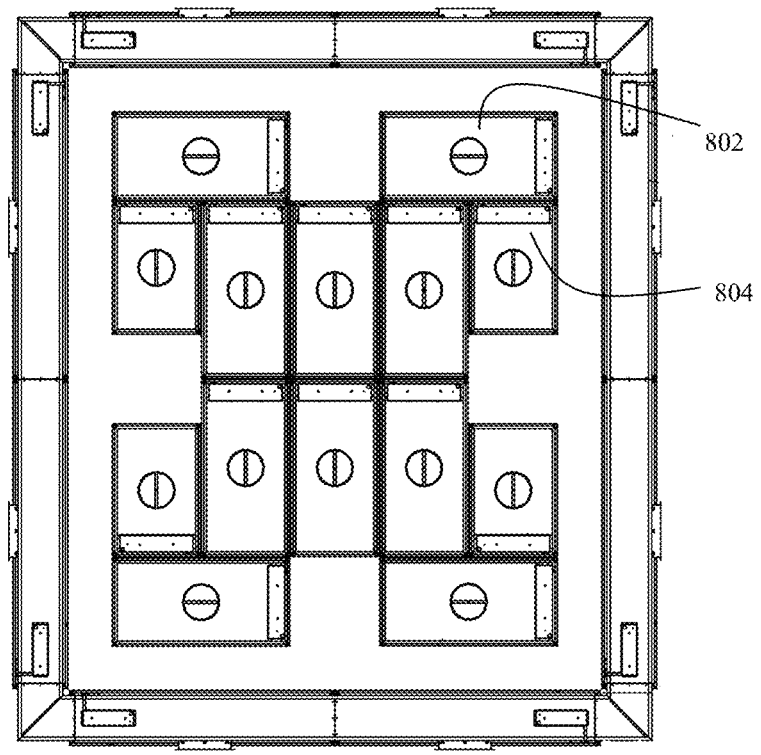
FIG. 8B shows a view of the interior of the laminar array portion of the ceiling mounted structural device when all of the perforated panels of its various laminar air flow systems have been removed.

FIG. 8B shows a view of the plenum which provides air to the laminar array. Essentially, this can also be considered to be a view of a portion of the interior of the ceiling mounted structural device (101) when all of the perforated panels (102a) of the mounted laminar air flow systems have been removed. Each laminar air flow system (102) has its own damper and air supply connection (802). Note that dampers (802) need not be equipped with actuators, and need not be computer operated dampers (although in some embodiments, they may be) since air to the system can be controlled by other dampers, such as damper BTD-1 shown in FIG. 3.

Some details of the LED drivers (804) used to drive the LED lighting system are also shown.

FIG. 9A shows a long axis side view of an individual laminar air flow system module (102). Here more details of the air supply connection and damper (802) and the LED drivers (804) may be seen. In some embodiments, modules such as the Krueger Sterilfo System®, Sterilflex™ system, or alternative systems, may be used.

In some embodiments, the laminar air flow system may also include UV lights configured to provide further UV sterilization to the incoming HEPA filtered air. In some embodiments, UV sterilizing systems such as Steril-Aire UVC emitter system, produced by Steril-Aire, Inc. may be used.

FIG. 9B shows a view looking up at the face of an individual air flow system module (102). Here details of the perforated wall structure (102a) and LED lighting (102) may be seen.

FIG. 9C shows a short axis side view of an individual laminar air flow system module (102). This shows a detail of the air supply connection and damper (802) from a different perspective.

Further discussion of the intelligent platform (ORICK) embodiment of the present invention.

The operating rooms of today, worldwide, are generally designed and used for a very clean level environment. However, they remain inherently unclean, even 'dirty', due to the very nature of the operating environment: numerous personnel, including surgeons, anesthesiologists, nurses, radiologists, and various types of equipment can enter and exit the operating room, and each event represents another way in which sterility can be compromised. In order to maintain the highest feasible levels of sterility, it would be desirable if the operating room was suitably configured so that the movement of humans, materials, and equipment could be automatically monitored and tracked. This way, information containing the movement of OR personnel, equipment and supplies can be stored in a database, and the data analyzed and compared to patient outcomes. Individuals, supplies, and equipment that are found to be correlated with unusual risks of HAI can be assessed, and appropriate corrective action can be initiated. Thus, in some embodiments, the systems and methods described herein can also comprise an information platform. This information platform can, for example, be configured to use real-time video cameras or other type sensors, which may be affixed or embedded in the chamber walls, to continuously collect (and store) data on the locations or status of various personnel, supplies, and equipment inside the operating room. Other types of cameras and scanners, such as hyperspectral cameras, cameras and illuminating systems optimized to image nucleic acids, proteins, or other biomarkers may also be used.

Although, in some embodiments, the ORICK aspects of the invention, described below, can be implemented in a chamber that is not equipped with the previously described automatic sterilization devices and methods, in a preferred embodiment, the ORICK aspects of the invention will be implemented in at least a simplified healthcare chamber (such as FIG. 1, 100), equipped with at least some automatic sterilizing devices and methods.

Figure 10:
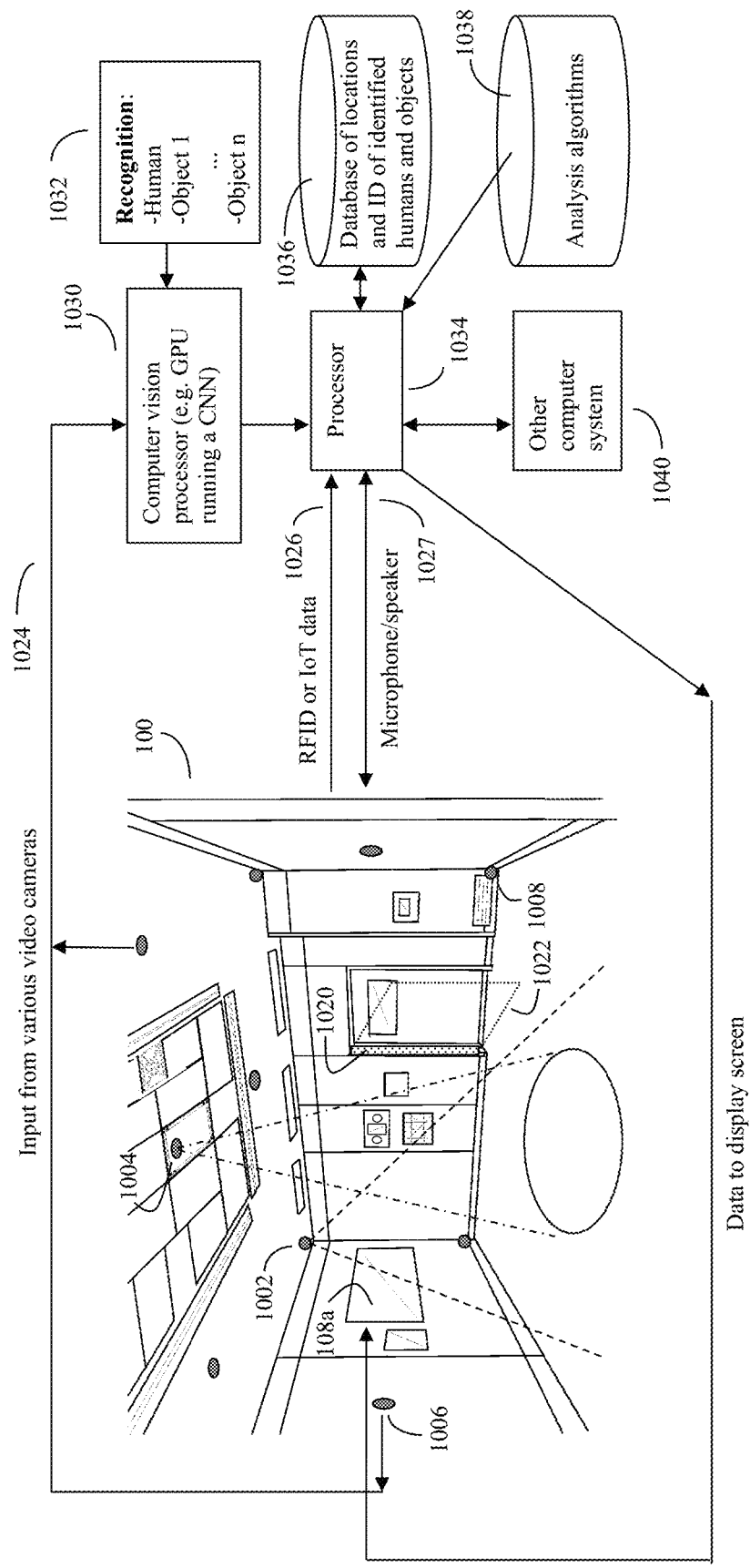
FIG. 10 shows an overview of an intelligent platform embodiment of the system. In this embodiment, a plurality of video cameras are mounted along many of the chamber walls, and the output of these video cameras analyzed using a computer vision system.

FIG. 10 shows an overview of an intelligent platform embodiment of the system. In this embodiment, at least one, and typically a plurality of video cameras (1002, 1004, 1006, 1008) may be mounted along many of the chamber walls, and the output of these video cameras analyzed using a computer vision system (1030). Usually, this computer vision system will be configured to at least recognize the presence and locations of humans in the chamber (100), usually as a function of time, with good time resolution. That is, ideally the location of humans and identified equipment in the chamber should be updated at least once a second, and preferably quicker, such as at higher of every 1/10 second, 1/15 second, 1/30 second or faster.

In some embodiments, the simplified chamber (100) equipped with automatic sterilizing devices and methods will also comprise a healthcare chamber system configured to reduce the risk of HAI. This simplified chamber may also comprise at least one computer processor and at least one sensor, but will also comprise computer memory as well. Although certain other aspects of the simplified healthcare chamber may be omitted in some embodiments, in a typical embodiment, this simplified chamber will also be configured to return interior air from the chamber by using at least one return air damper. The chamber (100) will also typically comprise air impermeable chamber walls, ceiling, and floor as before. The chamber will also typically comprise a laminar air flow system configured to blow HEPA filtered and UV (or hydroxyl generator) sterilized supply air over a defined field in the chamber. This laminar air flow system will typically be connected to at least one supply air damper. As before, the chamber will often be configured to obtain interior air by using the laminar air flow system to obtain sterilized outside air and blow HEPA filtered and UV (or hydroxyl generator) sterilized supply air over a defined field in the chamber. Further, the laminar air flow system will typically be connected to at least one supply air damper.

In the ORICK embodiment of the invention, as before, at least one computer processor and at least one sensor are also configured to verify that no humans are present in the chamber, and prior to a start of a sterilization cycle when no humans are present, to restrict access to the chamber. However, in the ORICK embodiment, often this at least one sensor will comprise at least one video camera, and often a plurality of video cameras (e.g. at least one of 1002, 1004, 1006, 1008). Further, in the ORICK embodiment, a more capable computer processor will often be used. This more capable computer processor can any of a computer vision system optimized computer processor (1030) and a standard computer processor (1034). Either may be configured to recognize humans in the chamber. Although, in this disclosure, certain specialized computer processors, such as GPU, will be used as an example of a computer vision system processor (1030), the present techniques may be implemented on any of one or a plurality of different computer processors.

In the simplified chamber (100), as per parent application Ser. No. 15/236,888, often at least one computer processor is also configured to isolate an interior air flow in the chamber from the outside air by closing at least one return damper and at least one supply air damper. Further, at least one computer processor is often also configured to activate an air phase anti-microbial agent generator. This generator is typically configured to fill the chamber with air phase anti-microbial agents at a time and dose level configured to kill at least a substantial majority of microbes in the chamber. Further, although not required, at least one computer processor is often also configured to deactivate the generator, and to flush remaining air phase anti-microbial agents from the chamber by at least opening the return damper and at least one supply air damper.

In FIG. 10, assume that the intelligent platform (ORICK) embodiment is implemented in the operating room type chamber (100), such as previously discussed in FIGS. 1 and 2. This chamber (100) is further configured with at least one (and usually a plurality of) video cameras (1002, 1004, 1006, 1008, etc.). These video cameras will often be mounted on, or embedded intothe walls, ceiling, corners, and even the floor of the chamber (100), and will preferably be positioned so that, at least by combining video feeds from all of the cameras, all areas of the room can be imaged, even when interfering equipment (e.g. operating tables, carts) is present in the room.

Put alternatively, in the ORICK embodiment of the invention, at least one sensor typically comprises a plurality of video cameras affixed or embedded in any of the air impermeable chamber walls, celling, and floor. This plurality of video cameras is typically configured to image substantially all of an interior of the chamber (100).

The video cameras may be any combination of wide-angle or narrow-angle cameras. In FIG. 10, the field of view of the video camera (1002) positioned in one upper corner of the operating room, and video camera (1004) positioned above the location of the operating table (not shown), are shown by the dashed lines. In some embodiments, video cameras may also be positioned above tables or cart locations so that equipment and optical codes (e.g. bar codes, QR codes, and the like) may be better observed by the system.

Put alternatively, in some versions of the ORICK embodiment of the invention, any of the computer vision system and at least one computer processor may be configured to recognize a presence of bar codes, QR codes, and other printed information on any of the various recognized humans and/or other objects in the chamber. The system can be also be configured to use these recognized bar codes, QR codes, and other printed information to label, in at least the computer memory (1036), at least some of the recognized humans and other objects in the chamber.

Although the computer vision system may be configured to recognize humans, various human faces, and other objects (such as certain types of equipment, tools and supplies), it would be useful if the system could be configured to distinguish additional information, such as tool identification numbers, manufacturing lot numbers, and the like. Although some of this information may be obtained by configuring the system to recognize optical codes (bar codes, QR codes, lettering), optical methods alone may not always be enough. Thus, in some embodiments, the system's intelligent platform may also comprise one or more wireless identification devices, such as RFID tag detectors, Internet of Things (IoT) wireless gateways (IoT detectors), and the like.

Put alternatively, in at least some embodiments, at least one sensor can further comprise at least one RFID sensor, IoT wireless gateway, or other wireless transceiver such as a Bluetooth or Wi-Fi, or Zigbee transceiver. Here, for conciseness, we will primarily discuss RFID detectors (sensors) and RFID tags as a specific example. However, this example should be considered to encompass detection of at least IoT devices as well.

Generally, any of the computer vision system (1030) and the computer processor (1034) (if separate from the computer vision system) can be configured to correlate detection of RFID signals with any of the recognized humans and other objects in the chamber. These detected RFID signals can be also used by the one or more processors to label, in at least the computer memory (1036), any of the recognized humans and other objects in the chamber.

Note again that, as previously discussed, IoT devices may also be detected by the system. IoT devices are often configured for wireless communications using Bluetooth or Wi-Fi wireless communications protocols. In addition to serving as an alternative type of identification tag, IoT devices may also be used for environmental sensors, medical equipment sensors, medical equipment control, hospital asset inventory management, usage, and the like. These medical equipment sensors can include surgical table (for pad or positioning), surgical robot, laparoscopic video, c-arm X-ray system images and the like, and the invention may be configured to receive data from such equipment by Wi-Fi, Bluetooth, Ethernet, or other wired or wireless method.

In some embodiments, the system can be configured so that standard pre-operative procedures can be further augmented with a system displayed surgeon 'pilot checklist' that can help assure the right equipment is available for the planned patient and procedure.

In some embodiments, for example, the invention may also be configured to use data from a surgical table to track how long a patient is in a certain position, as well as pad pressure zones to help detect and potentially warn in advance of potential injury. The invention may also keep track of suitable sensors to monitor tourniquet time, motions of surgical robots (e.g. to track actions and to help monitor when such robots may need cleaning/sterilization), monitor surgical microscopes, and handle other information from medical equipment and sensors as well.

FIG. 10 shows an embodiment where an RFID tag reader (1020) is positioned near the chamber entrance door. This can be configured to read RFID tags (often attached to either humans, equipment, or supplies) entering the room by scanning a field such as (1022). The RFID tag data can then be transmitted (1026) to a suitable processor (e.g. 1030, 1034) for further analysis.

The information from the various video cameras (1024) will often be fed to a computer vision system. As will be discussed in further detail shortly, this can be one or more computer processors (1030) such as a GPU configured to run deep convolution neural network methods (CNN) using the TensorFlow software framework, or other methods. These types of methods are often considered to be a type of "artificial intelligence" technique. The computer vision system will typically also comprise software configured to recognize various classes of objects, such as humans, different types of surgical tools, different types of surgical supplies, operating room carts, equipment, and the like (e.g. objects 1 . . . n). This object recognition configuration/CNN training software is shown as (1032).

Although computer processor (1030) will often be located on or near chamber (100), computer processor (1030) may be mounted elsewhere in the facility housing chamber (100), or even remotely (e.g. on a remote internet server, such as a "cloud" server) if desired.

Put alternatively, and as will be discussed in further detail shortly, in some embodiments, the computer vision system (1030) can comprise a trainable neural network that can be configured or reconfigured (1032) to recognize any of humans and a plurality of other objects in the chamber.

In some embodiments, the same computer vision processor (1030) used to implement vision recognition may also be used to perform other functions, up to and including even running the chamber itself. Thus, in some embodiments, the computer vision processor may be used to implement previously discussed computer processor control unit (110). However, in some embodiments it may be desirable to mount the computer vision processor (1030) separately from (110) because processor (1030) will be performing more computationally intensive loads, and thus may be bulkier, or may generate more heat, than a more standard general-purpose processor more commonly used for (110).

In some embodiments, less computationally intensive operations, such as receiving RFID codes, storing and retrieving data from databases, and interfacing with outside computer systems may be performed on more general-purpose processors (e.g. x86, MIPS, ARM, PowerPC, etc. processors (1034). However again, the computational workload may be divided among various permutations and types of computer processors, and thus the designation of certain processors as "GPU", "general purpose", and the like is not intended to be limiting.

In the embodiment shown in FIG. 10, the computer vision processor is thus recognizing various objects (humans, surgical tools) from the various video cameras, and passing the locations and identity of the recognized objects to processor (1034). Processor (1034) then associates any recognized objects with RFID codes (or optical codes), and, among other functions, may store the position of the various recognized objects, as a function of time, into database (1036).

Put alternatively, in some embodiments, any of the computer vision system (1030) and the computer processor (1034) may be further configured to record changes in locations (inside the chamber) of the recognized humans and other objects. The system can also be configured to accumulate data, such as statistical data, regarding the locations of these recognized humans and other objects in the chamber.

In some embodiments, as will be discussed in more detail in FIGS. 11A, 11B, 12A, and 12B, the intelligent platform embodiment of the invention may also analyze the incoming data versus various analysis algorithms (also referred to in the alternative as facility policies) to determine when exceptions (e.g. deviations from proper procedures) may have occurred.

FIG. 11A shows an example of how the chamber's video cameras and computer vision system can recognize the presence and locations of various humans, such as the patient and various personnel, in the chamber as a function of time. In some embodiments, the system may be configured to use facial recognition to determine which humans are present. In other embodiments, the system may use RFID tags, optical code recognition, or other methods to attempt to further identify which specific humans are present. When specific humans that are known to the system are found, the human's status (e.g. surgeon, anesthesiologist, nurse, etc.) can then be automatically assigned as well. The system can also be configured to automatically also verify that the specific human has proper authorization to be present. Those humans that the system can recognize as humans, but cannot specifically identify, can still be flagged as unidentified humans. Depending on the exception criteria, the presence of unidentified humans in the chamber during a scheduled operation can also be automatically flagged as an exception. In this case, at the 11:15 AM time point, the computer vision system recognizes that another human has entered the chamber, but this latest human is unidentified. The intelligent platform has thus flagged (and stored in memory) that this latest person is unidentified.

FIG. 11B shows an example of how, by storing a record of the position and location of various identified and unidentified humans and objects as a function of time, certain operating room "exceptions" can be automatically detected and flagged by the system. This record corresponds to the events shown above in FIG. 11A. Here assume that the system has used an RFID reader or optical recognition method to identify one recognized human as the patient (1102 shown horizontally on an operating table that is not shown), and other recognized humans as the surgeon, anesthesiologist, and two nurses. The times and locations of these humans are also recorded in memory, preferably at least once a second. In this example, at 11:15 AM, the positions of the identified persons are as expected. The surgeon (Dr. X) is located by the head of the operating table, the patient is on the table, the anesthesiologist (Dr. Y) was properly at the anesthesiologist's station, and the two nurses were each at their expected locations (n1 and n2 station).

The system has also detected that at 11:15 AM, surgical tool "A" (ID #4567) suddenly appears by the nurse's station n1. This might be expected if nurse 1 (Ms. A) has unwrapped the tool from a sterile container, and thus is not unexpected. The system has also detected that at 11:20, the location of tool "A" is now by the patient, suggesting that surgical tool "A" is being used (possibly by Surgeon 1) on the patient. This again is to be expected.

Occasionally, however, sales representatives for surgical equipment manufacturers may (possibly without full authorization) enter an operating room in order to demonstrate a new surgical tool to the surgeon. Such practices, if adequately documented and approved, can be acceptable, but if not adequately documented and approved, may be problematic. Here the intelligent platform aspects of the invention can be used to identify such situations.

In this example, the system has detected that an unknown individual (such as the sales representative for a medical device company), has also entered the chamber at 11:15 AM. The system recognizes this new object as a human (1104). But this unknown person is not wearing any type of detectable tag, and face recognition (if implemented) also cannot determine who this person is. The system can identify the object as a human, but cannot determine the human's identity, so automatically lists this person as "Unknown".

In this example, further assume that the system's computer vision system is also configured (e.g. trained) to use computer vision recognize at least certain types of surgical tools and supplies. Those surgical tools and supplies that are also identified by suitable RFID tags or optical markings can also be automatically identified. Depending on the amount of information stored on the tag or marking, the system can recognize a tool, and with appropriate tag data, can even identify the ID number of this specific, tool or supply.

In this example, the system has also used computer vision to identify that a surgical tool has entered the chamber at 11:15 AM. However, there is no RFID tag or other type tag. The system thus records that an unknown tool was also first detected in the chamber at 11:15 AM. This is at the same time and location that the unknown person also entered the chamber. If the system is configured with suitable analysis algorithms, the system can automatically determine that the position of this unknown tool generally tracks the same position as the unknown person.

Moreover, the system can be configured to use computer vision to also automatically detect, by tracking the position of the various humans, that between 11:20 and 11:25 AM, this unknown person and the unknown tool then were moved to be by the head of the operating table. This would not commonly be expected by the system. Even more unexpectedly. Surgeon 1 (Dr. X) has surprisingly now moved to the foot of the operating table. The identified tool "A'" is now in the same location as a waste container.

This scenario suggests that an unknown person, without adequate documentation, and using an undocumented tool, may have performed an otherwise undocumented surgical procedure on the patient. The underlying explanation may be innocent enough, perhaps a sales representative was demonstrating a new and more effective surgical tool. But if the patient gets an unexpected post-surgical infection (HAI), then this information may be very important. Indeed, if the hospital policy is not to allow this sort of thing, the system may be configured to automatically, and in real-time, trigger an "exception", "notice", or alarm here.

Here, a facility policy, such as: "if, during an operation, an unidentified person is near a patient on an operating table, and this person is associated with an unidentified tool, then automatically report an exception" could be used by the system processors to flag this type of situation.

This type of system can also be used to help improve the sterility of the chamber as well. For example, operating rooms are sometimes heavily booked during the day, with back-to-back operations. As a result, some facilities managers may prefer to set the chamber to only implement a full automatic sterilization cycle during breaks in the schedule, such as during the evenings. During back-to-back surgeries, these managers may instead use a human clean-up crew to clean up the chamber (operating room) between operations. This allows for efficient scheduling, but creates more opportunities for breaches in sterility.

However, in ORICK configured healthcare chambers, the ORICK system can also be configured to monitor the presence and identities of the various members of the clean-up crew. If the normal crew is present at the normal locations, the system can analyze this according to the system policies and automatically determine that all may be well. However, if the system identifies, between operations, that known clean-up crew members are absent, or unidentified persons are present, or that the locations of the clean-up crew members did not correspond to all of the proper clean-up locations in the chamber, then there may be a problem. There the system can again automatically check the observation data versus the facilities policies, and potentially identify a violation of the chamber (operating room) policies. The system may then indicate that a potential clean-up exception has occurred. The system can transmit a notice of the problem, recommend additional manual cleaning, indicate that the operating room is unavailable, and/or recommend (or even automatically trigger) an additional sterilization cycle as appropriate.

In this situation, the system can use an automated facility policy such as: "If, between operations, identified cleaning crew are not observed in those portions of the operating room designated for cleaning, then automatically report an exception".

Here, the general principle is that the system can be configured to automatically recognize and (often specifically identify) the locations over time of various persons and equipment. The system can then automatically compare this information to a database of facility (e.g. operating chamber) specific policies as to what patterns of activity are acceptable, and what patterns of activity may not be acceptable. The system can also be configured to automatically trigger exception notifications and/or other actions when unacceptable patterns of activity are observed.

In some embodiments, it may be useful to further configure the intelligent platform to interface with other computer systems (1040), such as hospital information management systems, BACnet (building automation and control) networks, and the like. The system can, for example, be configured to export data regarding various "exceptions" to a hospital information management system. The system can also, for example, be configured to receive patient information from outside systems, and display it on chamber screens (108a).

The system can also be configured to automatically correlate patient HAI data (usually obtained from outside medical databases, such as electronic medical records or EMI) with its database of appearance and locations of labeled objects in the operating room (1036). This may help the system develop rules determining which events are statistically associated with higher or lower rates of patient HAI.

In some embodiments, when the chamber must coordinate its operation with other systems, such as airflow, heating, and lighting systems within a larger building, the system may be configured to use BACnet or similar type building network to better coordinate the operations of the chamber with overall building operations.

Thus, in some embodiments, the invention's ORICK system's computer vision system and computer processor may be further configured to perform any of:

Display at least portions of the accumulated data, such as statistical data, regarding the locations of these recognized humans and other objects in the chamber on at least one display screen (such as 108a) mounted either on an interior chamber wall, and/or exterior to the chamber.

Export at least portions of the accumulated data, such as statistical data, to an outside computer system (1040).

Obtain imported data from the outside computer system (1040), and display at least some of this imported data on at least one display screen (such as 108a) mounted either on an interior chamber wall, and/or exterior to the chamber.

Figure 12A:
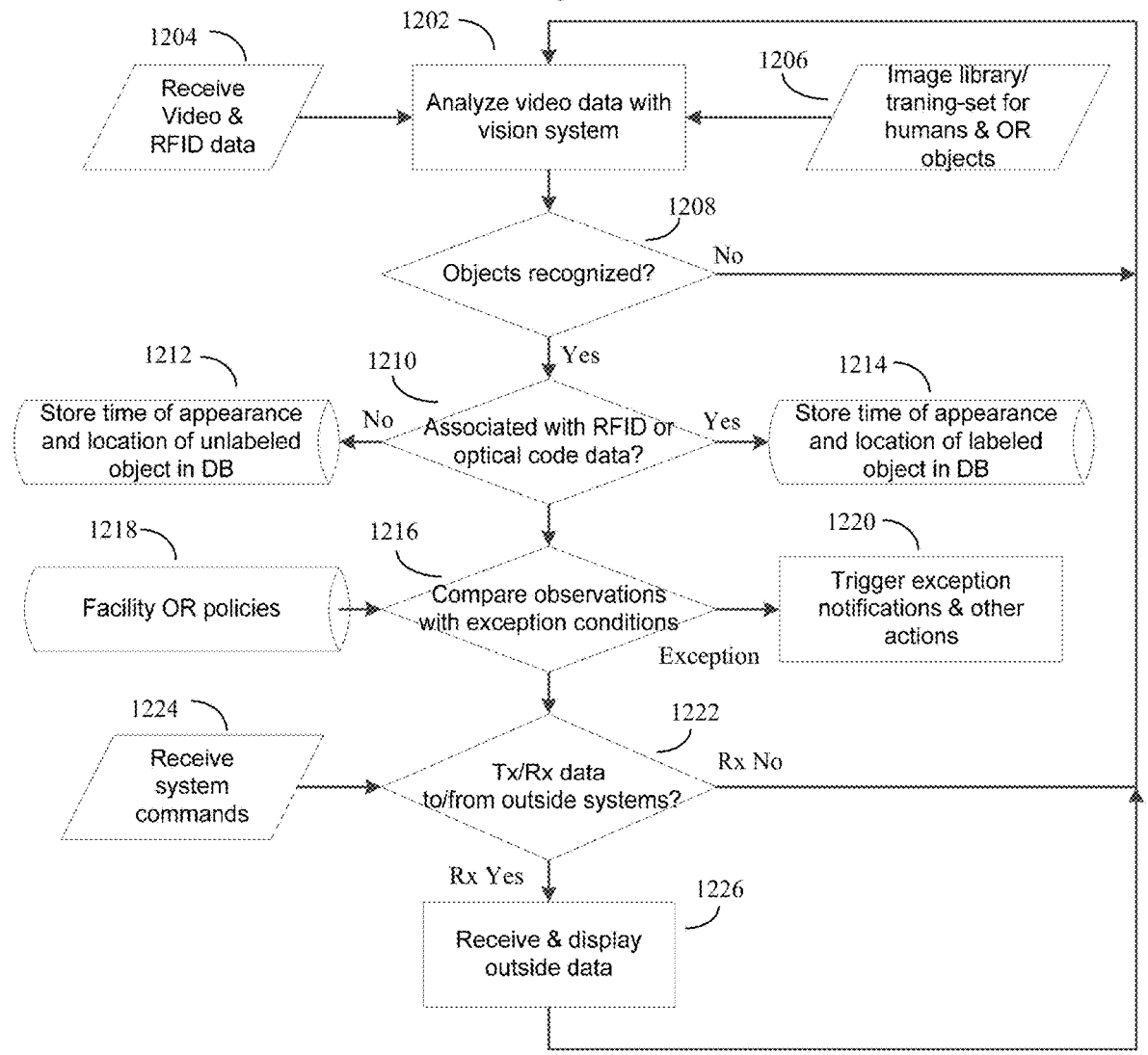
FIG. 12A shows a software flow chart showing an embodiment of the intelligent platform embodiment of the invention.

FIG. 12A shows a software flow chart showing an embodiment of the intelligent platform embodiment of the invention.

Here data, such as video (1024) and RFID data (1026) is received (1204), and is typically analyzed with a computer vision system using any of processors (1030) and (1034) at step (1202).

The computer vision system can recognize humans using various techniques, some of which are more computationally intensive (often requiring more specialized computer processors such as GPU 1030), and some of which are less computationally intensive (and can be run on standard computer processors such as 1034). The less computationally intensive methods include the methods of Viola and Jones, "*Rapid Object Detection using a Boosted Cascade of Simple Features*", ACCEPTED CONFERENCE ON COMPUTER VISION AND PATTERN RECOGNITION 2001. Other computationally less intensive methods include the Haar cascade object detection available in the OpenCV computer vision library, and the Histograms of Oriented Gradients (HOG) method, described by Dalal and Triggs in: "*Histograms of Oriented Gradients for Human Detection*", Pattern Recognition (CVPR '05), June 2005, San Diego, United States. pp. 886-893, ff10.1109/CVPR.2005.177f.

However, in a preferred computer vision embodiment, more computationally intensive methods based on deep convolution neural network methods (CNN) may be preferable. Although often requiring more specialized computer processors, the CNN methods have the advantage that they can be configured (e.g. trained) to recognize and classify many types of objects (e.g. humans, various types of operating room equipment, and the like). Such CNN methods are embodied in the popular TensorFlow open source software (API), produced by Google LLC.

Such TensorFlow CNN software can run on commercially available computer processors. These processors include various GPU processors, such as the Titan V processor produced by NVidia corporation, Google's tensor processing units (TPU), suitably configured FPGA chips and the like. Other computer processors, such as Intel Xeon processors, Neural Network Processors (NNP), and the like may also be used. Typically, the CNN will be trained or configured to recognize humans and other objects of interest (surgical tools, surgical supplies, operating room equipment) and the like using standard CNN object recognition techniques (1206). In a preferred embodiment, the system will be configured to image and recognize objects several times per second, preferably at video or near video speeds.

As bio-burden visualization systems improve, these camera system sensors will be incorporated into this invention as well, to further identify real time infectious microbes.

If the system is not seeing any changes in the objects (i.e. no one is present, and the equipment is just sitting there), then the system will often just remain in an idle mode, and keep looking for some sort of change.

However, if the system recognizes that new objects have appeared (1208), in a preferred embodiment, the computer vision system will seek to classify the objects, and also attempt to specifically identify the objects using optical or RFID or IoT data. Here, for example, if the system determines that an object appears proximate an RFID scanner at the same time that an RFID code is detected, the system may associate the RFID code data with the object (1210). Alternatively, if the system detects that the recognized object is also carrying an optical code such as a bar code, QR code, or even alphanumeric code, then these optical codes may also be associated with the object, and stored as a labeled object in the system database (1214). Some objects may be identified and classified, but contain no detectable codes, and will thus be stored in the system database as a recognized but unlabeled object. Facial recognition may also be used as appropriate, but since operating room personnel often wear masks, its utility may be limited. Thus, use of optical or RFID tags may often be preferred.

The system will typically then compare (1216) the computer vision observations against a database of analysis algorithms (1038), such as various chamber facility (e.g. operating room) policies (1218). These policies can include various chamber cleaning and maintenance policies, as well as various chamber operating policies. Examples of chamber cleaning policies can include specifications that humans should be observed at various defined locations in the chamber, or associated with various types of chamber equipment, during a specified manual cleaning or maintenance situation. The policies will, of course, also specify that before and during an automated sterilization cycle, no humans may be in the chamber, and additionally may also specify that certain types of equipment should either be in the chamber, or not be in the chamber. The automated vision system may also be configured to observe various environmental indicators inside of the chamber, such as visual indicators of air flow, temperature, and even chemical environment (e.g. visual indicators of levels of hydrogen peroxide), and confirm that an automated sterilization cycle has been performed according to the facility policies (1218). Here, if the system detects an exception (e.g. non-conformance to the policies/algorithms), the system can trigger exception notifications (1220), and other actions as well. For example, the system, upon observing evidence of improper cleaning or sterilization, may schedule additional sterilization cycles or schedule maintenance. IoT equipped environmental sensors, and other types of IoT devices, may also be detected and recorded as well.

Put alternatively, in some embodiments, the system (ORICK equipped environmental chamber) can further comprise at least one visual or IoT environmental indicator affixed or embedded in any of the air impermeable chamber walls, celling, and floor. This at least one visual or IoT environmental indicator will typically be configured to produce an environmental indicator visual signal, or IoT wireless signal, that varies according to a chamber environment, and will also typically be configured to be imaged by at least one of the chamber's video cameras or detected by at least one of the chambers wireless IoT detectors, such as a Bluetooth or Wi-Fi transceiver. In this embodiment, the computer vision system (1030) or computer processor is typically further configured to record changes in this at least one environmental indicator visual signal or IoT signal. In this embodiment, any of the computer vision system and the computer processor are also configured to correlate changes in this at least one environmental indicator visual or IoT signal with changes in the chamber's environment.

Additionally, as previously discussed, the intelligent platform (ORICK) embodiment of the invention may also be configured to monitor conditions inside the chamber while it is being used as an operating room. At any time, the system may also be configured, either automatically, or upon command, to simply store the video camera output in memory as video files as well.

Here, as previously discussed, the facility policies can monitor (1216) for problematic occurrences during an operation, and trigger exception notifications and action (1220) here as well. The system may post notification on a chamber display screen (108*a*), sound audio warnings. Video recordings from the camera may be preserved in memory for future analysis. Data regarding the exception may be transmitted to outside systems. The system may also schedule additional chamber sterilizing cycles as appropriate.

In some embodiments, it may be useful to configure the system to respond to commands, such as verbal commands, from various personnel (1224). Here standard audio pickups and automated speech recognition devices and methods may be used. These commands may, for example, direct the system to receive data from outside computer systems (1040), (1226), and display this data on various display devices such as device (108*a*). The system can also be configured to transmit data to outside computer systems as well. These outside computer systems may comprise outside computers running medical databases with electronic medical records (EMI), be connected to computer systems associated with vendors or repair/maintenance systems, governmental regulatory agencies, reimbursement (insurance) agencies, administrative computer systems, accounting computer systems, telemedicine systems (e.g. to allow outside physicians to consult), and the like.

Figure 12B:
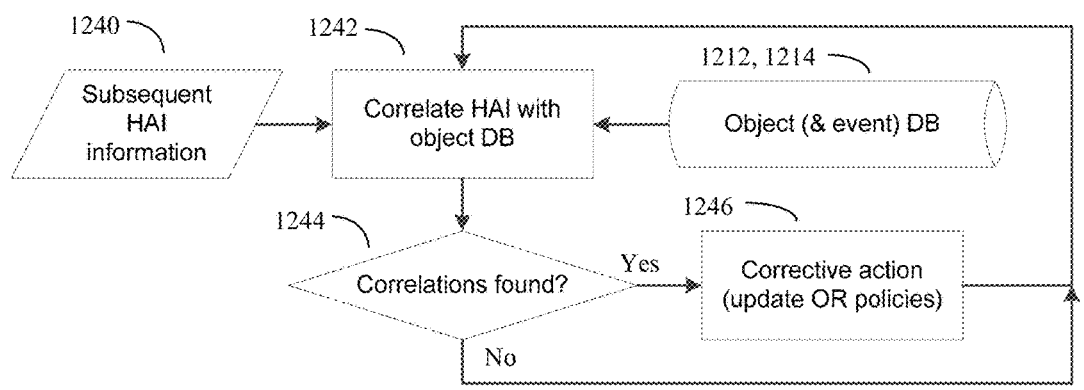
FIG. 12B shows how the system records may be compared to subsequently observed HAI information, and situations that correlate with higher levels of HAI can be used to further refine the system's facility policies (e.g. analysis algorithms) and other types of corrective action.

FIG. 12B shows how the system records may be compared to subsequently observed HAI information, and situations that correlate with higher levels of HAI can be used to further refine the system's facility policies, and other types of corrective action.

It will typically take hours, days, or even weeks to detect any hospital-acquired infections (HAI) that occur due to adverse events in the operating room. By that time, the patient will usually often be long removed from the chamber (100). Thus, in order to ensure that the system is operating according to the best possible algorithms (1038) or facility policies (1218), the invention may, in some embodiments, further employ methods to "close the loop" and correlate observed operating room events with subsequent HAI.

This correlation process can be done with standard statistical correlation methodology, or with more advanced machine learning methods. In either case, subsequently obtained HAI information (1240), which may be obtained from outside computer systems (1040), can be automatically correlated (1242) against the previously obtained database of objects and events (1212, 1214). When significant correlations are found (1244), the system can implement various types of corrective action (1246). Occasionally, this corrective action may include updating the facility (operating room) policies/algorithms (1218, 1038) that the system uses to automatically detect exceptions or adverse events (1216).

These correlations may occasionally find unexpected results. For example, the system may automatically detect that a combination of a particular surgeon and a particular surgical tool is associated with a significantly higher rate of HAI or other adverse events. This may happen, for example, if a particular surgeon is not adequately trained or competent using a particular surgical tool. Similarly, a particular member of the cleaning staff may also be associated with an unusually high rate of HAI. In either case, the system may be configured to detect future occurrences of any such events, and trigger appropriate exception notifications and other events (1220).

Note that although as previously described, the above intelligent platform or ORICK system and methods can be implemented using a simplified version of the chamber, the ORICK system and methods can also be implemented in more full-featured versions of the chamber as well. Thus, for example, in some embodiments, the air phase anti-microbial agent generator may further be a combination generator and humidifier configured to operate by regulating humidity, and configured to convert an aqueous solution of hydrogen peroxide into air phase hydrogen peroxide by using any of a misting, nebulizer based, vaporizing based, or aerosol generating type device. Further, the chamber may further comprise a ceiling mounted structural device comprising a load bearing structure. In this embodiment, the laminar air flow system may be mounted on this structural device. As previously discussed, often the chamber will be an operating room, and the defined field in the chamber may be an operating table.

Use Examples and Benefits

Identification and Monitoring of Patient and Operating Room Personnel

As previously discussed, by using RFID, IoT, optical or other automatically readable badges, all patients and personnel in the chamber (e.g. the operating room, or OR) can be monitored. This includes patient identification upon entering the OR and leaving the OR. Surgical team identification upon entering and leaving the chamber, as well as tracking of movements within the OR. The presence of other visitors (observing MD's, observing students, observing or demonstrating equipment manufacturers, etc.) in the OR can also be tracked as well.

By automatically identifying and tracking all chamber personnel, the invention can improve the likelihood of successful outcomes and improve the best practices of operating room procedures.

The system's computer processor can also be configured to immediately match the patient ID with the scheduled procedure, ensuring that the patient is actually the person scheduled. With suitable computer vision, if the system is informed about the specifics of any given operation, the system could also monitor the progress of the operation, and indicate an exception if the observed progress of the operation was not consistent with the preset operation specifics.

In some embodiments, the invention may be configured to import the patient's electronic medical record from another computer system (1040) and display this on the chamber's display screen (108*a*). With suitable voice recognition hardware (e.g. audio microphones, and speakers 1027) and software, the invention may also be configured to automatically, or with voice command, call up the patient's medical information, (e.g. last MRI or CT Scan), for display, as well as to respond to all other types of voice commands as well. In some embodiments, with suitable software, the computer processor monitoring the audio pickup may be configured to recognize unusual sounds (e.g. alarms, unusual mechanical sounds, and the like), and register these as an exception as well.

Increased Use of RFID and IoT Device Tracking within the OR

As the surgical world more fully embraces RFID and IoT device implementation, the system may also be configured to monitor all suitably tagged surgical instruments and supplies in the chamber. In some embodiments, the system processor may also be configured to communicate the equipment status with outside computer systems (1040) and help insure the quality and safety of these items.

Pro-Active Air Flow Management.

In some embodiments, the system will be configured to continually track door openings, the number, movement, and type of personnel in the OR. This information can be correlated with HAI information (see FIG. 12B) and used to help determine what combination air flows, door openings, and personnel movement are associated with better or worse HAI outcomes. This information can be used to provide suitable analysis algorithms (1038) and or Facility OR policies (1218) which, when combined with the system observations (1216), can provide real-time alerts to surgical teams and other personnel when high HAI risk conditions are observed.

User Group Examples

Various different types of chamber user groups could use the system data for a variety of different purposes, including obtaining real-time actionable data, periodic summaries, forming best practices (e.g. facility policies), continuous learning, and further improvement of the system's various image recognition and other algorithms. These groups can include cleaning staff, surgical staff, and even patients (e.g. as a supplement to the patient electronic medical record). The information can also be used for chamber scheduling, re-certification, insurance, best practices analysis, training, equipment vendors, asset management, accounting, hospital planning, and administrative purposes at all levels of administration. In some embodiments, the system may be configured to output this type of data according to various user interfaces, such as dashboards, graphical summaries, tabular data, and the like. Additionally, the massive amounts of digital data from the invention's sensors can be input to various types of external AI engines (such as IBM's Watson system, Google, AWS system, and the like) for further assessments.

Sterilflex™ is a trademark, and Sterilfo System® is a registered trademark, of Lau Industries, Inc., a Delaware Corporation.

The invention claimed is:

1. A healthcare chamber system configured to reduce a risk of HAI, said system comprising:
   at least one computer processor, computer memory, and at least one sensor;
   a chamber configured to return interior air from said chamber by using at least one return air damper, said chamber comprising air impermeable chamber walls, ceiling, and floor;
   said chamber further comprising a laminar air flow system;
   said laminar air flow system configured to blow HEPA filtered and UV sterilized supply air over a defined field in said chamber;
   said laminar air flow system connected to at least one supply air damper;
   said chamber configured to obtain interior air by using said laminar air flow system to obtain sterilized outside air and blow HEPA filtered and UV sterilized supply air over a defined field in said chamber;
   said laminar air flow system connected to said at least one supply air damper;
   said at least one computer processor and at least one sensor configured to verify that no humans are present in said chamber, and prior to a start of a sterilization cycle when no humans are present to restrict access to said chamber;
   said at least one computer processor also configured to isolate an interior air flow in said chamber from outside air by closing at least one return damper and at least one supply air damper;
   said at least one computer processor also configured to activate an air phase anti-microbial agent generator, said generator configured to fill said chamber with air phase anti-microbial agents at a time and dose level configured to kill at least a substantial majority of microbes in said chamber;
   said at least one computer processor also configured to deactivate said generator, and to flush remaining air phase anti-microbial agents from said chamber by at least opening said return damper and said at least one supply air damper.

2. The system of claim 1, wherein said at least one sensor comprises at least one video camera; and any of a computer vision system and said at least one computer processor are configured to recognize humans in said chamber.

3. The system of claim 2, wherein said at least one sensor comprises a plurality of video cameras affixed or embedded in any of said air impermeable chamber walls, celling, and floor, said plurality of video cameras configured to image substantially all of an interior of said chamber.

4. The system of claim 2, wherein said computer vision system comprises a trainable neural network that can be reconfigured to recognize any of humans and a plurality of other objects in said chamber.

5. The system of claim 2, wherein any of said computer vision system and said computer processor are further configured to record changes in locations of said recognized humans and other objects in said chamber, and to accumulate data regarding said locations of said recognized humans and other objects in said chamber.

6. The system of claim 5, wherein any of said computer vision system and said at least one computer processor are configured to recognize a presence of bar codes, QR codes, and other printed information on any of said recognized humans and other objects in said chamber; and to use said recognized bar codes, QR codes, and other printed information to label, in at least said computer memory, at least some of said recognized humans and other objects in said chamber.

7. The system of claim 5, wherein any of said computer vision system and said computer processor is further configured to perform any of:
a) display at least portions of said accumulated data on at least one display screen mounted either on an interior chamber wall, and/or exterior to said chamber;
b) export at least portions of said accumulated data to an outside computer system;
c) obtain imported data from said outside computer system, and display at least some of said imported data on said at least one display screen mounted either on an interior chamber wall, and/or exterior to said chamber.

8. The system of claim 2, wherein said at least one sensor further comprises at least one RFID or IoT sensor, and any of said computer vision system and said computer processor is configured to correlate detection of RFID or IoT signals with any of said recognized humans and other objects in said chamber, and to use said detected RFID or IoT signals to label, in at least said computer memory, any of said recognized humans and other objects in said chamber.

9. The system of claim 2, further comprising at least one visual or IoT environmental indicator affixed or embedded in any of said air impermeable chamber walls, ceiling, and floor, said at least one visual or IoT environmental indicator configured to produce an environmental indicator signal that varies according to a chamber environment, and also configured to be detected by any of at least one said video cameras or a wireless IoT detector;
said an of said computer vision system and said compute processor further configured to record changes in said at least one environmental indicator visual signal or IoT signal; and
any of said computer vision system and said computer processor is configured to correlate said changes in said at least one environmental indicator visual signal or IoT signal with changes in said chamber environment.

10. The system of claim 1, wherein said air phase antimicrobial agent generator is a combination generator and humidifier configured to operate by regulating humidity, and configured to convert an aqueous solution of hydrogen peroxide into air phase hydrogen peroxide by using any of a misting, nebulizer based, vaporizing based, or aerosol generating type device;
said chamber further comprising a ceiling mounted structural device comprising a load bearing structure, said laminar air flow system mounted on said structural device; and
said chamber is an operating room, and said defined field in said chamber is an operating table.

11. A healthcare chamber system configured to reduce a risk of HAI, said system comprising:
at least one computer processor, computer memory, and at least one sensor;
a chamber configured to return interior air from said chamber by using at least one return air damper, said chamber comprising air impermeable chamber walls, celling, and floor;
wherein said at least one sensor comprises a plurality of video cameras affixed or embedded in any of said air impermeable chamber walls, celling, and floor, said plurality of video cameras configured to image substantially all of an interior of said chamber;
wherein any of a computer vision system and said at least one computer processor are configured to recognize any of humans and other objects in said chamber;
wherein any of said computer vision system and said computer processor is further configured to record changes in locations of any of said recognized humans and other objects in said chamber, and to accumulate data regarding any of said locations of said recognized humans and other objects in said chamber;
said chamber further comprising a laminar air flow system;
said laminar air flow system configured to blow HEPA filtered and UV sterilized supply air over a defined field in said chamber;
said laminar air flow system connected to at least one supply air damper;
said chamber configured to obtain interior air by using said laminar air flow system to obtain sterilized outside air and blow HEPA filtered and UV sterilized supply air over a defined field in said chamber;
said laminar air flow system connected to said at least one supply air damper;
said at least one computer processor and at least one sensor configured to verify that no humans are present in said chamber, and prior to a start of a sterilization cycle when no humans are present to restrict access to said chamber;
said at least one computer processor also configured to isolate an interior air flow in said chamber from outside air by closing at least one return damper and at least one supply air damper;
said at least one computer processor also configured to activate an air phase anti-microbial agent generator, said generator configured to fill said chamber with air phase anti-microbial agents at a time and dose level configured to kill at least a substantial majority of microbes in said chamber;
said at least one computer processor also configured to deactivate said generator, and to flush remaining air phase anti-microbial agents from said chamber by at least opening said return damper and said at least one supply air damper.

12. The system of claim 11, wherein said computer vision system comprises a trainable neural network that can be reconfigured to recognize any of humans and a plurality of other objects in said chamber.

13. The system of claim 11, wherein any of a computer vision system and said at least one computer processor are configured to recognize a presence of bar codes, QR codes, and other printed information on any of said recognized humans and other objects in said chamber; and to use said recognized bar codes, QR codes, and other printed information to label, in at least said computer memory, any of said recognized humans and other objects in said chamber.

14. The system of claim 11, wherein any of said computer vision system and said computer processor is further configured to perform any of:
   a) display at least portions of said accumulated data on at least one display screen mounted either on an interior chamber wall, and/or exterior to said chamber;
   b) export at least portions of said accumulated data to an outside computer system;
   c) obtain imported data from said outside computer system, and display at least some of said imported data on said at least one display screen mounted either on an interior chamber wall, and/or exterior to said chamber.

15. The system of claim 11, wherein said at least one sensor further comprises at least one RFID or IoT sensor, and any of said computer vision system and said computer processor is configured to correlate detection of RFID or IoT signals with any of said recognized humans and other objects in said chamber, and to use said detected RFID or IoT signals to label, in at least said computer memory, any of said recognized humans and other objects in said chamber.

16. The system of claim 11, further comprising at least one visual environmental indicator affixed or embedded in any of said air impermeable chamber walls, celling, and floor, said at least one visual environmental indicator configured to produce an environmental indicator visual signal that varies according to a chamber environment, and also configured to be imaged by at least one of said plurality of video cameras; and
   said computer vision system further configured to record changes in said at least one environmental indicator visual signal; and
   any of said computer vision system and said computer processor is configured to correlate said changes in said at least one environmental indicator visual signal with changes in said chamber environment.

17. The system of claim 11, wherein said air phase anti-microbial agent generator is a combination generator and humidifier configured to operate by regulating humidity, and configured to convert an aqueous solution of hydrogen peroxide into air phase hydrogen peroxide by using any of a misting, nebulizer based, vaporizing based, or aerosol generating type device;
   said chamber further comprising a ceiling mounted structural device comprising a load bearing structure, said laminar air flow system mounted on said structural device; and
   said chamber is an operating room, said defined field in said chamber is an operating table.

18. A healthcare chamber system configured to reduce a risk of HAI, said system comprising:
   at least one computer processor, computer memory, and at least one sensor;
   a chamber configured to return interior air from said chamber by using at least one return air damper, said chamber comprising air impermeable chamber walls, celling, and floor;
   wherein said at least one sensor comprises a plurality of video cameras affixed or embedded in any of said air impermeable chamber walls, celling, and floor, said plurality of video cameras configured to image substantially all of an interior of said chamber;
   wherein any of a computer vision system and said at least one computer processor are configured to recognize humans and other objects in said chamber;
   wherein any of said computer vision system and said computer processor are further configured to record changes in locations of any of said recognized humans and other objects in said chamber, and to accumulate data regarding any of said locations of said recognized humans and other objects in said chamber;
   said chamber further comprising a ceiling mounted structural device comprising a load bearing structure, with a laminar air flow system-mounted on said structural device;
   said laminar air flow system configured to blow HEPA filtered and UV sterilized supply air over a defined field in said chamber;
   said laminar air flow system connected to at least one supply air damper;
   said chamber configured to obtain interior air by using said ceiling mounted structural device and said laminar air flow system to obtain sterilized outside air and blow HEPA filtered and UV sterilized supply air over a defined field in said chamber;
   said laminar air flow system connected to said at least one supply air damper;
   said at least one computer processor and at least one sensor configured to verify that no humans are present in said chamber, and prior to a start of a sterilization cycle when no humans are present to restrict access to said chamber;
   said at least one computer processor also configured to isolate an interior air flow in said chamber from outside air by closing at least one return damper and at least one supply air damper;
   said at least one computer processor also configured to activate an air phase anti-microbial agent generator, said generator configured to fill said chamber with air phase anti-microbial agents at a time and dose level configured to kill at least a substantial majority of microbes in said chamber;
   said at least one computer processor also configured to deactivate said generator, and to flush remaining air phase anti-microbial agents from said chamber by at least opening said return damper and said at least one supply air damper.

19. The system of claim 18, wherein any of said computer vision system and said at least one computer processor are configured to recognize a presence of bar codes, QR codes, and other printed information on any of said recognized humans and other objects in said chamber; and to use any of said recognized bar codes, QR codes, and other printed information to label, in at least said computer memory, any of said recognized humans and other objects in said chamber; and/or
   wherein said at least one sensor further comprises at least one RFID or IoT sensor, and any of said computer vision system and said computer processor is configured to correlate detection of RFID or IoT signals with any of said recognized humans and other objects in said chamber, and to use said detected RFID or IoT signals to label, in at least said computer memory, any of said recognized humans and other objects in said chamber.

20. The system of claim 19, wherein said computer vision system comprises a trainable neural network that can be reconfigured to recognize any of humans and a plurality of other objects in said chamber; and wherein any of said computer vision system and said computer processor is further configured to perform any of:
a) display at least portions of said accumulated data on at least one display screen mounted either on an interior chamber wall, and/or exterior to said chamber;
b) export at least portions of said accumulated data to an outside computer system;
c) obtain imported data from said outside computer system, and display at least some of said imported data on said at least one display screen mounted either on an interior chamber wall, and/or exterior to said chamber.

21. The system of claim 18, wherein said system is further configured to use any of real time or and stored data from said at least one sensor for any of reducing levels of HAI, improving patient safety, and improving efficiency.

\* \* \* \* \*